United States Patent
Barbaric et al.

(10) Patent No.: US 12,063,981 B2
(45) Date of Patent: Aug. 20, 2024

(54) METHODS AND SYSTEMS FOR HEATING CARRIER MATERIAL USING A VAPORIZER

(71) Applicant: Airgraft Inc., Montreal (CA)

(72) Inventors: Mladen Barbaric, Westmount (CA); Kisae Kim, Westmount (CA); Sungmoon Kim, Brossard (CA); Bong Geun Kim, Candiac (CA); Chongchun Moon, La Prairie (CA); Nathan Songa Yapi, Montreal (CA); Luca Corbellini, Montreal (CA)

(73) Assignee: Airgraft Inc., Montreal (CA)

( * ) Notice: Subject to any disclaimer, the term of this patent is extended or adjusted under 35 U.S.C. 154(b) by 139 days.

(21) Appl. No.: 16/993,164

(22) Filed: Aug. 13, 2020

(65) Prior Publication Data

US 2021/0045452 A1 Feb. 18, 2021

Related U.S. Application Data

(60) Provisional application No. 62/886,244, filed on Aug. 13, 2019.

(51) Int. Cl.
| | |
|---|---|
| *A24F 40/57* | (2020.01) |
| *A24F 40/65* | (2020.01) |
| *A61M 15/00* | (2006.01) |

(52) U.S. Cl.
CPC .............. *A24F 40/57* (2020.01); *A24F 40/65* (2020.01); *A61M 15/0091* (2013.01);
(Continued)

(58) Field of Classification Search
CPC ...................................................... A24F 40/57
See application file for complete search history.

(56) References Cited

U.S. PATENT DOCUMENTS

| | | |
|---|---|---|
| 4,756,318 A | 7/1988 | Clearman et al. |
| D299,066 S | 12/1988 | Newell |
| | (Continued) | |

FOREIGN PATENT DOCUMENTS

| | | |
|---|---|---|
| CA | 2805553 C | 1/2015 |
| CA | 3083248 A1 | 5/2019 |
| | (Continued) | |

OTHER PUBLICATIONS

International Search Report issued for PCT/CA2019/051326 mailed on Nov. 21, 2019.
(Continued)

*Primary Examiner* — Cynthia Szewczyk
(74) *Attorney, Agent, or Firm* — Cooley LLP

(57) ABSTRACT

In some embodiments, a system includes a mouthpiece defining a mouthpiece opening, a reservoir configured to contain carrier material, a heating assembly including a heating element configured to apply heat to the carrier material, and a control assembly. The control assembly is configured to receive target temperature data based, at least in part, on an identity of the carrier material contained in the reservoir. The control assembly is further configured to, upon receiving an indication that a user is applying suction to the mouthpiece opening of the mouthpiece, apply a current to the heating element of the heating assembly such that a temperature of the carrier material disposed near the heating element rises to a predetermined temperature based on the target temperature data.

19 Claims, 10 Drawing Sheets

(52) U.S. Cl.
CPC .............. *A61M 2205/3368* (2013.01); *A61M 2205/3553* (2013.01); *A61M 2205/3653* (2013.01)

(56) References Cited

U.S. PATENT DOCUMENTS

| | | |
|---|---|---|
| 4,947,874 A | 8/1990 | Brooks et al. |
| 5,044,550 A | 9/1991 | Lamm |
| 5,060,671 A | 10/1991 | Counts et al. |
| 5,095,921 A | 3/1992 | Losee et al. |
| 5,105,831 A | 4/1992 | Banerjee et al. |
| 5,135,009 A | 8/1992 | Muller et al. |
| 5,179,966 A | 1/1993 | Losee et al. |
| 5,226,411 A | 7/1993 | Levine |
| 5,249,586 A | 10/1993 | Morgan et al. |
| 5,388,594 A | 2/1995 | Counts et al. |
| 5,408,574 A | 4/1995 | Deevi et al. |
| 5,564,442 A | 10/1996 | MacDonald et al. |
| 5,915,387 A | 6/1999 | Baggett, Jr. et al. |
| 6,053,176 A | 4/2000 | Adams et al. |
| D449,404 S | 10/2001 | Emery |
| 6,501,052 B2 | 12/2002 | Cox et al. |
| 6,513,524 B1 | 2/2003 | Storz |
| 6,532,965 B1 | 3/2003 | Abhulimen et al. |
| 6,701,921 B2 | 3/2004 | Sprinkel, Jr. et al. |
| 7,096,896 B2 | 8/2006 | Py |
| D610,303 S | 2/2010 | Valle |
| 7,832,410 B2 | 11/2010 | Hon |
| D634,892 S | 3/2011 | Hein |
| 7,997,280 B2 | 8/2011 | Rosenthal |
| D677,000 S | 2/2013 | Liu |
| D683,844 S | 6/2013 | Andrade et al. |
| 8,499,766 B1 | 8/2013 | Newton |
| D689,818 S | 9/2013 | Sasada |
| 8,528,569 B1 | 9/2013 | Newton |
| 8,689,804 B2 | 4/2014 | Fernando et al. |
| 8,707,965 B2 | 4/2014 | Newton |
| 8,733,346 B2 | 5/2014 | Rinker |
| 8,897,628 B2 | 11/2014 | Conley et al. |
| 8,991,402 B2 | 3/2015 | Bowen et al. |
| 9,078,473 B2 | 7/2015 | Worm et al. |
| 9,084,440 B2 | 7/2015 | Zuber et al. |
| 9,308,336 B2 | 4/2016 | Newton |
| D762,003 S | 7/2016 | Lomeli |
| 9,408,416 B2 | 8/2016 | Monsees et al. |
| D765,908 S | 9/2016 | Zahr et al. |
| D770,090 S | 10/2016 | Zahr et al. |
| D770,091 S | 10/2016 | Zahr et al. |
| 9,459,021 B2 | 10/2016 | Greim et al. |
| D771,308 S | 11/2016 | Saydar et al. |
| 9,516,899 B2 | 12/2016 | Plojoux et al. |
| D776,338 S | 1/2017 | Lomeli |
| 9,549,573 B2 | 1/2017 | Monsees et al. |
| D778,235 S | 2/2017 | Geier et al. |
| 9,596,887 B2 | 3/2017 | Newton |
| 9,717,276 B2 | 8/2017 | Brammer et al. |
| 9,820,509 B2 | 11/2017 | Newton et al. |
| 9,894,938 B2 | 2/2018 | Vick et al. |
| D812,289 S | 3/2018 | Ward et al. |
| 10,058,130 B2 | 3/2018 | Monsees et al. |
| 10,070,669 B2 | 3/2018 | Monsees et al. |
| D816,267 S | 4/2018 | Fornarelli |
| 9,943,114 B2 | 4/2018 | Batista |
| 9,949,507 B2 | 4/2018 | Flick |
| 9,986,767 B2 | 6/2018 | Batista et al. |
| 9,999,250 B2 | 6/2018 | Minskoff et al. |
| D825,102 S | 8/2018 | Bowen et al. |
| D827,117 S | 8/2018 | Rigbi |
| 10,045,567 B2 | 8/2018 | Monsees et al. |
| 10,045,568 B2 | 8/2018 | Monsees et al. |
| 10,058,124 B2 | 8/2018 | Monsees et al. |
| 10,058,129 B2 | 8/2018 | Monsees et al. |
| 10,076,139 B2 | 9/2018 | Monsees et al. |
| 10,104,915 B2 | 10/2018 | Bowen et al. |
| 10,111,470 B2 | 10/2018 | Monsees et al. |
| 10,117,465 B2 | 11/2018 | Monsees et al. |
| 10,117,466 B2 | 11/2018 | Monsees et al. |
| 10,130,780 B2 | 11/2018 | Talon |
| 10,159,282 B2 | 12/2018 | Monsees et al. |
| 10,201,185 B2 | 2/2019 | Bleloch et al. |
| 10,201,190 B2 | 2/2019 | Monsees et al. |
| 10,206,429 B2 | 2/2019 | Davis et al. |
| D842,536 S | 3/2019 | Bowen et al. |
| D844,235 S | 3/2019 | Cividi |
| D844,240 S | 3/2019 | Kauss |
| 10,219,543 B2 | 3/2019 | Gill et al. |
| 10,231,486 B2 | 3/2019 | Bowen et al. |
| 10,244,793 B2 | 4/2019 | Monsees et al. |
| 10,247,443 B2 | 4/2019 | Flick |
| 10,264,823 B2 | 4/2019 | Monsees et al. |
| 10,271,578 B2 | 4/2019 | John et al. |
| D849,996 S | 5/2019 | Duque et al. |
| 10,279,934 B2 | 5/2019 | Christensen et al. |
| 10,334,883 B2 | 7/2019 | Silvestrini et al. |
| 10,362,806 B2 | 7/2019 | Cadieux et al. |
| 10,375,994 B2 | 8/2019 | Mironov et al. |
| 10,405,582 B2 | 9/2019 | Hatton et al. |
| 10,426,196 B2 | 10/2019 | Calfee et al. |
| 10,440,989 B2 | 10/2019 | Gardella et al. |
| 10,499,685 B2 | 12/2019 | Prestia et al. |
| 10,524,980 B2 | 1/2020 | Naing et al. |
| 10,568,357 B2 | 2/2020 | Metrangolo et al. |
| 10,588,337 B2 | 3/2020 | Prestia et al. |
| 10,595,565 B2 | 3/2020 | Hu et al. |
| 10,602,776 B2 | 3/2020 | Batista |
| 10,609,958 B2 | 4/2020 | Robinson et al. |
| 10,645,973 B2 | 5/2020 | Silvestrini et al. |
| 10,721,971 B2 | 7/2020 | Barbaric et al. |
| 10,729,176 B2 | 8/2020 | Vasiliev et al. |
| 10,750,782 B2 | 8/2020 | Batista |
| 10,757,975 B2 | 9/2020 | Batista et al. |
| 10,772,352 B2 | 9/2020 | Mishra et al. |
| 10,820,620 B2 | 11/2020 | Saygili |
| 10,822,123 B2 | 11/2020 | Barbaric et al. |
| 10,834,968 B2 | 11/2020 | John et al. |
| 10,856,575 B2 | 12/2020 | Gill et al. |
| 10,856,576 B2 | 12/2020 | Mironov et al. |
| 10,856,583 B2 | 12/2020 | Fursa et al. |
| 10,863,766 B2 | 12/2020 | Sutton et al. |
| 10,863,770 B2 | 12/2020 | Mironov et al. |
| 10,863,775 B2 | 12/2020 | Silvestrini |
| 10,869,504 B2 | 12/2020 | Mironov et al. |
| 10,881,144 B2 | 1/2021 | Batista et al. |
| 10,888,123 B2 | 1/2021 | Silvestrini et al. |
| 10,973,263 B2 | 4/2021 | Fursa |
| 11,039,644 B2 | 6/2021 | Paprocki et al. |
| 11,044,950 B2 | 6/2021 | Collett et al. |
| 11,051,545 B2 | 7/2021 | Batista et al. |
| 11,058,141 B2 | 7/2021 | Sanna et al. |
| 11,064,725 B2 | 7/2021 | Wilke et al. |
| 11,090,450 B2 | 8/2021 | Li et al. |
| 11,129,410 B2 | 9/2021 | Barbaric et al. |
| 11,140,923 B2 | 10/2021 | Courbat et al. |
| 11,154,086 B2 | 10/2021 | Griscik et al. |
| 11,154,670 B2 | 10/2021 | Saygili |
| 11,160,309 B2 | 11/2021 | Mironov et al. |
| 11,166,492 B2 | 11/2021 | Robinson et al. |
| 11,178,899 B2 | 11/2021 | Schaller et al. |
| 11,197,498 B2 | 12/2021 | Waller et al. |
| 11,200,770 B2 | 12/2021 | Hubbard et al. |
| 11,202,466 B2 | 12/2021 | Prestia et al. |
| 11,202,467 B2 | 12/2021 | Malgat |
| 11,206,864 B2 | 12/2021 | Hejazi |
| 11,241,032 B2 | 2/2022 | Garcia Garcia et al. |
| 11,252,992 B2 | 2/2022 | Blandino et al. |
| 11,272,731 B2 | 3/2022 | Zuber et al. |
| 11,272,738 B2 | 3/2022 | Zuber et al. |
| 11,311,051 B2 | 4/2022 | Mironov et al. |
| 11,350,664 B2 | 6/2022 | Alston et al. |
| 11,357,258 B2 | 6/2022 | Robinson et al. |
| 11,375,754 B2 | 7/2022 | Batista |
| 11,390,403 B2 | 7/2022 | Barbaric et al. |
| 11,399,564 B2 | 8/2022 | Rossoll et al. |
| 11,406,132 B2 | 8/2022 | Zuber et al. |

(56) References Cited

U.S. PATENT DOCUMENTS

| | | |
|---|---|---|
| 11,406,136 B2 | 8/2022 | Barbaric et al. |
| 11,425,926 B2 | 8/2022 | Pijnenburg et al. |
| 11,452,313 B2 | 9/2022 | Kaufman et al. |
| 11,457,664 B2 | 10/2022 | Aoun et al. |
| 11,478,016 B2 | 10/2022 | John et al. |
| 11,510,291 B2 | 11/2022 | Horrod et al. |
| 11,510,870 B1 | 11/2022 | White |
| 11,516,894 B2 | 11/2022 | Gill |
| 11,528,931 B2 | 12/2022 | Sanna et al. |
| 11,606,976 B2 | 3/2023 | Sanna et al. |
| 11,632,978 B2 | 4/2023 | Rojo-Calderon et al. |
| 11,659,863 B2 | 5/2023 | Blandino et al. |
| 11,673,375 B2 | 6/2023 | Dietmann et al. |
| 2003/0106551 A1 | 6/2003 | Sprinkel et al. |
| 2004/0182389 A1 | 9/2004 | Sprinkel et al. |
| 2010/0112815 A1 | 5/2010 | O'Dougherty et al. |
| 2011/0277761 A1 | 11/2011 | Terry et al. |
| 2013/0284192 A1 | 10/2013 | Peleg et al. |
| 2013/0319439 A1 | 12/2013 | Gorelick et al. |
| 2014/0299141 A1* | 10/2014 | Flick .............. H05B 1/0202 |
| | | 219/494 |
| 2014/0366898 A1 | 12/2014 | Monsees et al. |
| 2014/0378790 A1 | 12/2014 | Cohen |
| 2015/0090280 A1 | 4/2015 | Chen |
| 2015/0150308 A1 | 6/2015 | Monsees et al. |
| 2015/0181945 A1 | 7/2015 | Tremblay |
| 2015/0224268 A1 | 8/2015 | Henry et al. |
| 2015/0296887 A1 | 10/2015 | Zhu |
| 2015/0320116 A1 | 11/2015 | Bleloch et al. |
| 2016/0080535 A1 | 3/2016 | Stanimirovic et al. |
| 2016/0128384 A1 | 5/2016 | Luciani |
| 2016/0157524 A1 | 6/2016 | Bowen et al. |
| 2016/0200463 A1 | 7/2016 | Hodges et al. |
| 2016/0295917 A1 | 10/2016 | Malgat et al. |
| 2016/0309784 A1 | 10/2016 | Silvestrini et al. |
| 2016/0331031 A1 | 11/2016 | Malgat et al. |
| 2016/0338413 A1 | 11/2016 | Li et al. |
| 2016/0363917 A1 | 12/2016 | Blackley |
| 2016/0366947 A1 | 12/2016 | Monsees et al. |
| 2017/0042235 A1 | 2/2017 | Gorilovsky |
| 2017/0156399 A1 | 6/2017 | Freeman et al. |
| 2017/0208867 A1 | 7/2017 | Li et al. |
| 2017/0238610 A1* | 8/2017 | Reevell ............... G06F 1/04 |
| 2017/0238617 A1 | 8/2017 | Scatterday |
| 2018/0000157 A1 | 1/2018 | Batista et al. |
| 2018/0000160 A1* | 1/2018 | Taschner ............. A24F 40/40 |
| 2018/0037381 A1 | 2/2018 | White et al. |
| 2018/0043114 A1 | 2/2018 | Bowen et al. |
| 2018/0060873 A1 | 3/2018 | Chu |
| 2018/0077967 A1 | 3/2018 | Hatton et al. |
| 2018/0093054 A1 | 4/2018 | Bowen et al. |
| 2018/0104214 A1 | 4/2018 | Raichman |
| 2018/0117268 A1 | 5/2018 | Selby et al. |
| 2018/0177231 A1 | 6/2018 | Woodbine et al. |
| 2019/0158938 A1 | 5/2019 | Bowen et al. |
| 2019/0159519 A1 | 5/2019 | Bowen et al. |
| 2019/0183185 A1 | 6/2019 | Manas et al. |
| 2019/0204126 A1 | 7/2019 | Kane et al. |
| 2019/0261689 A1 | 8/2019 | Bowen et al. |
| 2019/0335817 A1 | 11/2019 | Freeman et al. |
| 2020/0029618 A1 | 1/2020 | Fraser et al. |
| 2020/0085105 A1 | 3/2020 | Barbaric et al. |
| 2020/0093172 A1 | 3/2020 | Liu |
| 2020/0113245 A1 | 4/2020 | Rosser et al. |
| 2020/0113246 A1 | 4/2020 | Barbaric et al. |
| 2020/0115073 A1 | 4/2020 | Barbaric et al. |
| 2020/0206430 A1 | 7/2020 | Woodbine et al. |
| 2020/0236994 A1 | 7/2020 | Blandino et al. |
| 2020/0245684 A1 | 8/2020 | Mironov et al. |
| 2020/0352224 A1 | 11/2020 | Plojoux et al. |
| 2021/0015148 A1 | 1/2021 | Shenton et al. |
| 2021/0045452 A1 | 2/2021 | Barbaric et al. |
| 2021/0046261 A1 | 2/2021 | Barbaric et al. |
| 2021/0084977 A1 | 3/2021 | Batista et al. |
| 2021/0100281 A1 | 4/2021 | Abi Aoun et al. |
| 2021/0120876 A1 | 4/2021 | Saleem et al. |
| 2021/0145076 A1 | 5/2021 | Barbaric et al. |
| 2021/0219386 A1 | 7/2021 | Atkins et al. |
| 2021/0235762 A1 | 8/2021 | Jochnowitz |
| 2021/0259309 A1 | 8/2021 | Taurino |
| 2021/0261277 A1 | 8/2021 | Barbaric et al. |
| 2021/0361890 A1 | 11/2021 | Li et al. |
| 2021/0401048 A1 | 12/2021 | Egoyants et al. |
| 2022/0030944 A1 | 2/2022 | Griscik et al. |
| 2022/0030954 A1 | 2/2022 | Rath et al. |
| 2022/0071266 A1 | 3/2022 | Fujikura et al. |
| 2022/0087311 A1 | 3/2022 | Han et al. |
| 2022/0104542 A1 | 4/2022 | Barbaric et al. |
| 2022/0117307 A1 | 4/2022 | Abi Aoun et al. |
| 2022/0125112 A1 | 4/2022 | Zuber et al. |
| 2022/0167663 A1 | 6/2022 | Paton et al. |
| 2022/0175015 A1 | 6/2022 | Jeong et al. |
| 2022/0225682 A1 | 7/2022 | Abi Aoun et al. |
| 2023/0148681 A1 | 5/2023 | Barbaric et al. |
| 2023/0294855 A1 | 9/2023 | Barbaric et al. |

FOREIGN PATENT DOCUMENTS

| | | |
|---|---|---|
| CA | 3086414 A1 | 6/2019 |
| CN | 204466911 U | 7/2015 |
| CN | 105962427 A | 9/2016 |
| CN | 107822208 | 3/2018 |
| CN | 110236228 A | 9/2019 |
| EP | 2592005 A1 | 5/2013 |
| EP | 3183979 B1 | 6/2018 |
| EP | 3183980 B1 | 8/2018 |
| EP | 3166426 B1 | 9/2018 |
| EP | 3311684 B1 | 3/2019 |
| EP | 3145345 B1 | 4/2019 |
| EP | 3160274 B1 | 5/2019 |
| EP | 3297459 B1 | 7/2019 |
| EP | 3409467 B1 | 7/2019 |
| EP | 3145338 B1 | 11/2019 |
| EP | 3240440 B1 | 11/2019 |
| EP | 3393281 B1 | 2/2020 |
| EP | 3393283 B1 | 2/2020 |
| EP | 3407942 B1 | 4/2020 |
| EP | 3407943 B1 | 4/2020 |
| EP | 3407947 B1 | 4/2020 |
| EP | 3442364 B1 | 4/2020 |
| EP | 3503747 B1 | 12/2020 |
| EP | 3364792 B1 | 3/2021 |
| EP | 3624618 B1 | 4/2021 |
| EP | 3634163 B1 | 4/2021 |
| EP | 3695735 B1 | 4/2021 |
| EP | 3599908 B1 | 5/2021 |
| EP | 3599910 B1 | 5/2021 |
| EP | 3599911 B1 | 5/2021 |
| EP | 3638057 B1 | 5/2021 |
| EP | 3679765 B1 | 7/2021 |
| EP | 3417727 B1 | 9/2021 |
| EP | 3760062 B1 | 9/2021 |
| EP | 3367828 B1 | 12/2021 |
| EP | 3957197 A1 | 2/2022 |
| EP | 3574710 B1 | 3/2022 |
| EP | 3716798 B1 | 3/2022 |
| EP | 3829351 B1 | 3/2022 |
| EP | 3639874 B1 | 4/2022 |
| EP | 3796793 B1 | 4/2022 |
| EP | 3145344 B2 | 6/2022 |
| EP | 3796791 B1 | 6/2022 |
| EP | 3809887 B1 | 6/2022 |
| EP | 3562332 B1 | 7/2022 |
| EP | 3638058 B1 | 8/2022 |
| EP | 3490392 B1 | 11/2022 |
| EP | 3826480 B1 | 11/2022 |
| EP | 3498051 B1 | 12/2022 |
| EP | 3478104 B1 | 3/2023 |
| EP | 3632244 B1 | 4/2023 |
| EP | 3970514 B1 | 7/2023 |
| EP | 3970517 B1 | 7/2023 |
| EP | 4030942 B1 | 7/2023 |
| FR | 3039039 A1 | 1/2017 |
| WO | WO-9527411 A1 | 10/1995 |

(56) References Cited

FOREIGN PATENT DOCUMENTS

| | | |
|---|---|---|
| WO | WO-9632854 A2 | 10/1996 |
| WO | WO-2011065028 A1 | 6/2011 |
| WO | WO-2016096745 A1 | 6/2016 |
| WO | WO-2017036954 A1 | 3/2017 |
| WO | WO 2017/139595 | 8/2017 |
| WO | WO 2017/185051 | 10/2017 |
| WO | WO 2017/187148 | 11/2017 |
| WO | WO-2017205692 A1 | 11/2017 |
| WO | WO 2018/024154 | 2/2018 |
| WO | WO-2018125889 A1 | 7/2018 |
| WO | WO 2019/082280 A1 | 5/2019 |
| WO | WO 2019/104227 | 5/2019 |
| WO | WO 2019/126805 | 6/2019 |
| WO | WO-2019114597 A1 | 6/2019 |
| WO | WO 2019/138043 | 7/2019 |
| WO | WO-2019152873 A1 * 8/2019 ............. A24F 40/51 |
| WO | WO 2019/204812 | 10/2019 |
| WO | WO-2020020603 A1 | 1/2020 |
| WO | WO-2020056510 A1 | 3/2020 |
| WO | WO-2020077454 A1 | 4/2020 |
| WO | WO-2020077455 A1 | 4/2020 |
| WO | WO-2020127107 A1 | 6/2020 |
| WO | WO-2020127116 A2 | 6/2020 |
| WO | WO-2020153830 A1 | 7/2020 |
| WO | WO-2021018836 A1 | 2/2021 |
| WO | WO-2021026660 A1 | 2/2021 |
| WO | WO-2021026661 A1 | 2/2021 |
| WO | WO-2021037826 A1 | 3/2021 |
| WO | WO-2021069525 A1 | 4/2021 |
| WO | WO-2021069526 A1 | 4/2021 |
| WO | WO-2021118186 A2 | 6/2021 |
| WO | WO-2022023777 A1 | 2/2022 |
| WO | WO-2022118009 A1 | 6/2022 |
| WO | WO-2022133611 A1 | 6/2022 |
| WO | WO-2022135992 A1 | 6/2022 |
| WO | WO-2022136598 A1 | 6/2022 |
| WO | WO-2022171762 A1 | 8/2022 |
| WO | WO-2022198337 A1 | 9/2022 |
| WO | WO-2022208831 A1 | 10/2022 |
| WO | WO-2022208832 A1 | 10/2022 |
| WO | WO-2022263851 A1 | 12/2022 |
| WO | WO-2022263862 A1 | 12/2022 |
| WO | WO-2023104706 A1 | 6/2023 |

OTHER PUBLICATIONS

International Search Report issued for PCT/CA2019/051468 mailed on Dec. 19, 2019.
International Search Report issued for PCT/CA2019/051469 mailed on Dec. 30, 2019.
International Search Report and Written Opinion issued for PCT/CA2020/051113, mailed Nov. 5, 2020.
International Search Report and Written Opinion issued for PCT/CA2020/051114, mailed Nov. 13, 2020.
Extended European Search Report and Search for European Application No. 19861746.6 Mailed on May 17, 2022, 10 pages.
International Search Report and Written Opinion for Application No. PCT/CA2022/050455 dated Jun. 20, 2022, 10 pages.
International Search Report and Written Opinion for International Application No. PCT/CA2021/051881 dated Feb. 23, 2022, 10 pages.
Communication, dated Jul. 11, 2022, for European Application No. 19873242.2 (11 total pages).
Extended European Search Report for Application EP19873242.2, mailed Oct. 12, 2022, 11 pages.
Invitation to Pay Fees for PCT/US2023/071800, mailed Nov. 10, 2023 12 pages.
Office Action for Japanese Application No. JP2021514432 dated Sep. 11, 2023, 15 pages.

* cited by examiner

| Phytocannabinoid | THC | Δ-8 THC | THCV | CBD | CBDA | CBDV | CBN | CBG | CBC |
|---|---|---|---|---|---|---|---|---|---|
| Boiling Point [°C] | 157 | 175-178 | 220 | 160-180 | 150 | 220 | 185 | 225 | 185 |
| Terpene | citronellol | d-limonene | humulene | humulene | linalool | B-caryophyllene | B-myrcene | B-pinene | terpineol-4-ol |
| Boiling Point [°C] | 225 | 177 | 124 | 106 | 198 | 119 | 167 | 167 | 209 |

300

METHODS AND SYSTEMS FOR HEATING CARRIER MATERIAL USING A VAPORIZER

CROSS-REFERENCE TO RELATED APPLICATIONS

This application claims priority to and the benefit of U.S. Provisional Application No. 62/886,244 filed Aug. 13, 2019, entitled "METHODS AND SYSTEMS FOR HEATING CARRIER MATERIAL USING A VAPORIZER," the entire contents of which are hereby expressly incorporated by reference for all purposes.

BACKGROUND

Electronic vapor delivery systems are increasingly popular. Such systems have been developed for inhalation-based delivery of *Cannabis* components and nicotine. Volatile substances (e.g., carrier materials and/or the substances carried by carrier materials) often have different boiling points, combustion points, and optimal vaporization temperatures, temperature ranges, and/or rates of temperature increase, which may depend in part on a desired dosage of the particular substances carried by the carried materials. Thus, there is a need for methods and systems for heating volatile substances such that each volatile substance can be vaporized at a proper and/or desired temperature for each respective volatile substance.

SUMMARY

In some embodiments, a control assembly of a vaporizer device can be configured to determine the contents of a carrier material within a capsule assembly coupled to the vaporizer device. Based, at least in part, on the specific constituent substances included in the carrier material and particular characteristics of the carrier material, the control assembly can determine a particular temperature or temperature range at which the carrier material is to be vaporized. Based on the particular temperature or temperature range at which the control assembly determines that the carrier material is to be vaporized, upon receiving an indication that a user is applying suction to a mouthpiece opening of the mouthpiece, the control assembly can apply a current to a heating element of the heating assembly such that the temperature of the carrier material disposed near the heating element rises to the particular temperature or to a temperature within the particular temperature range. During a period of continuous suction on the mouthpiece opening (e.g., a draw), the control assembly can continue to apply current to the heating element at intervals (e.g., predefined intervals) such that the temperature of the carrier material disposed near the heating element remains within the temperature range determined by the control assembly.

DETAILED DESCRIPTION

As the popularity of, and commercial interest in, electronic vapor delivery systems (also referred to as "vapor devices" or "vaporizers") such as electronic cigarettes ("e-cigs") continues to grow, their manufacture and distribution is becoming more globally widespread. Not every substance to be vaporized (e.g., carrier material), however, has the same viscosity and optimal vaporization temperature. Systems and methods for improved electronic vapor delivery, including temperature optimization are set forth herein.

In some embodiments, a system includes a mouthpiece defining a mouthpiece opening, a reservoir configured to contain carrier material, a heating assembly including a heating element configured to apply heat to the carrier material, and a control assembly. The control assembly is configured to receive target temperature data based, at least in part, on an identity of the carrier material contained in the reservoir. The control assembly is further configured to, upon receiving an indication that a user is applying suction to the mouthpiece opening of the mouthpiece, apply a current to the heating element of the heating assembly such that a temperature of the carrier material disposed near the heating element rises to a predetermined temperature based on the target temperature data.

In some embodiments, target temperature data (e.g., a heating profile) can be received by a control assembly based, at least in part, on an identity of a carrier material contained in a reservoir associated with a vaporizer. A current can be supplied at 1073 by the control assembly to a heating element associated with the vaporizer based on the target temperature data such that the carrier material is vaporized by the heating element according to the target temperature data.

In some embodiments, a system includes a mouthpiece defining a mouthpiece opening, a reservoir configured to contain carrier material, a heating assembly including a heating element configured to apply heat to the carrier material, and a control assembly. The control assembly is configured to determine the contents of the carrier material within the reservoir, determine a target temperature at which the carrier material is to be vaporized based, at least in part, on constituent substances included in the carrier material, and, upon receiving an indication that a user is applying suction to the mouthpiece opening of the mouthpiece, apply a current to the heating element of the heating assembly such that a temperature of the carrier material disposed near the heating element rises to the target temperature.

Figure 1A:
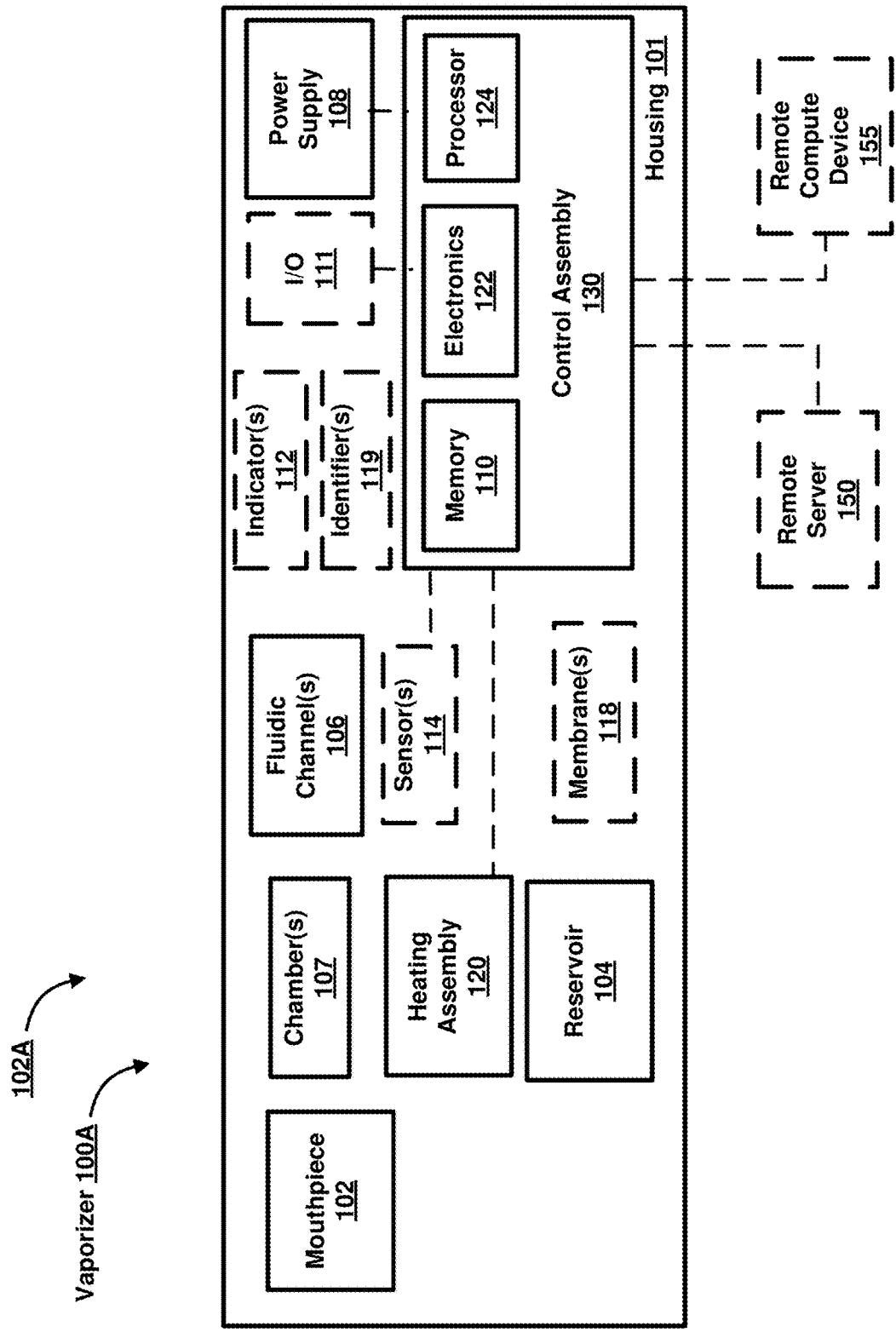
FIG. 1A is a schematic block diagram of a disposable vaporizer, according to an embodiment.

FIG. 1A is a schematic block diagram of a system 102A including a disposable (or "single-use") vaporizer, according to an embodiment. As shown in FIG. 1A, a disposable vaporizer 100A includes a mouthpiece 102, a precursor reservoir 104, one or more fluidic channels 106 (e.g., microfluidics or other passageways), a power supply 108, a heating assembly 120, and a control assembly 130. The disposable vaporizer 100A can also include one or more chambers 107. All of the components of the disposable vaporizer 100A can be disposed within a common (e.g., monolithic) housing 101. Optionally, the disposable vaporizer 100A also includes one or more of: an input/output (I/O) module 111, identifier(s) 119, sensor(s) 114, membrane(s) 118, and indicator(s) 112, also disposed within the common housing 101. The control assembly 130 can include a memory 110, electronics 122, and a processor 124 (e.g., coupled to a printed circuit board), and optionally can be configured to communicate with a remote server 150 and/or a remote compute device 155.

The mouthpiece 102 can comprise one or more of: ceramic, heat-resistant plastic, anodized aluminum, or any other suitable material. The power supply 108 can include any suitable battery or fuel cell, for example having high-drain characteristics. The precursor reservoir 104 can be in fluid communication with at least one of the mouthpiece 102, the one or more chambers 107 (e.g., vapor expansion chambers), and the fluidic channel(s) 106, such that carrier material can travel from the precursor reservoir 104 into a fluid path defined by the mouthpiece 102, the one or more chambers 107, and the fluidic channel(s) 106 as a result of triggering heating and vaporization of the carrier material. In some embodiments, heating of the carrier material can be initiated by the control assembly 130 in response to a user's sucking/drawing on the mouthpiece 102 during use (e.g., via activation of a pressure sensor of the sensor(s) 114). In some embodiments, the vaporizer 100A can include a mechanical interface (e.g., a button) (e.g., included in the input/output module 111) that the user can manually actuate to trigger the heating and vaporization of the carrier material.

The memory 110 can include any electronic component capable of storing electronic information. The term memory may refer to various types of processor-readable media such as random access memory (RAM), read-only memory (ROM), non-volatile random access memory (NVRAM), programmable read-only memory (PROM), erasable programmable read only memory (EPROM), electrically erasable PROM (EEPROM), flash memory, magnetic or optical data storage, registers, etc. Memory is said to be in electronic communication with a processor if the processor can read information from and/or write information to the memory. Memory that is integral to a processor is in electronic communication with the processor.

The input/output module 111 can include one or more of: a push-button control for causing vapor generation, a battery indicator, an electromechanical connector for charging and/or data communication, a light source (e.g., one or more light-emitting diodes), etc. The heating assembly 120 can include a heating element such as, for example, a coil heater, a rod-shaped heater, a pancake heater, a chemical heater, or any other heater that is sized, dimensioned, and constituted of material suitable for heating a carrier material. In some embodiments, for example, the heating assembly can include a ceramic cylindrical wick portion defining a central passageway, a coil coupled to and/or disposed within the cylindrical wick portion configured to heat the cylindrical wick portion, and a cotton wick portion wrapped around the outer surface of the cylindrical wick portion. In some embodiments, for example, the heating assembly can include a wick (e.g., a cotton wick) and a coil having a portion wrapped around the wick and two ends extending away from the wick. The two ends can be configured to be coupled to the control assembly 130 such that the temperature of the coil can be controlled, at least in part, by a current applied to the ends of the coil. The wick can be configured to transport carrier material toward a portion of the wick adjacent the coil.

The electronics 122 can include any suitable communication component configured to allow communication of information (e.g., data) to and/or from a remote compute device 155 and/or a remote server 150 to the control assembly 130 (e.g., to the processor 124). For example, the electronics 122 can include one or more of: a GPS receiver, an antenna, heater control circuitry (e.g., configured to control a temperature of the heating element of the heating assembly 120), or a transceiver for wireless (e.g., Bluetooth) communication with a command center or other remote compute device (such as a mobile device of a user). The sensor(s) 114 can include one or more of: a pressure sensor, a temperature sensor, a position sensor, an orientation sensor, etc. The identifier(s) 119 may include, for example, a bar code, a QR code, and/or a near-field communication (NFC) device such that the vaporizer 100A may be identified and/or recognized by an external device (e.g., the remote compute device 155).

The processor 124 can include one or more of: a general purpose processor, a central processing unit (CPU), a microprocessor, a digital signal processor (DSP), a controller, a microcontroller, a state machine and so forth. Under some circumstances, a "processor" may refer to an application specific integrated circuit (ASIC), a programmable logic device (PLD), a field programmable gate array (FPGA), etc. The term "processor" may refer to a combination of processing devices, e.g., a combination of a DSP and a microprocessor, a plurality of microprocessors, one or more microprocessors in conjunction with a DSP core or any other such configuration.

In some embodiments, the vaporizer 100A can include one or more additives combined with carrier material within the reservoir 104. The one or more additives can include one or more flavorants. The membrane(s) 118 can be disposed on an outer surface of the vaporizer 100A (e.g., within an opening defined by the housing 101) and arranged such that carrier material and/or additive can be supplied to the reservoir 104 via the membrane(s) 118. The membrane(s) 118 can include a valved impermeable or semi-permeable material, for example comprising a rubber, polyvinyl chloride (PVC), etc. The indicator(s) 112 can include one or more of: an illumination source (e.g., one or more light-emitting diodes), a speaker, a display screen, a haptic feedback component (e.g., a vibration element), etc.

In some embodiments, in use, the disposable vaporizer 100A is configured such that, when a user sucks, or "draws," on an opening defined by the mouthpiece, the resulting change in pressure within the vaporizer 100A is measured by a sensor (e.g., a pressure sensor) of the sensor(s) 114. In response to the sensor 114 sensing a change in pressure (e.g., above a threshold change in pressure or to a threshold pressure level), the processor 124 can actuate the heater control circuitry of the electronics 122 to pass a current through the heating element that is in contact with, or in sufficiently close proximity to, the carrier material or a wick material containing at least a portion of the carrier material, so as to cause the volatilization of a portion of the carrier material. One or more characteristics of the current or affecting the delivery of the current passed through the heating element (e.g., voltage, wattage) can be controlled by the processor 124 based on, for example, an ambient temperature measured by a temperature sensor of the sensor(s) 114, a resistance of the heating element, and/or a target temperature data (e.g., a heating profile or target temperature range) associated with the carrier material (e.g., as determined by the processor 124 and/or provided to the processor 124 prior to use). The volatilized carrier material, or vapor, travels toward the mouthpiece via one or more of the expansion chamber(s) and/or the fluidic channels and exits the vaporizer via the opening in the mouthpiece for inhalation by the user.

In some embodiments, the control assembly 130 can be coupled via a wired (e.g., Ethernet connection) or a wireless connection (e.g., via a WiFi network connection) to a remote server 150. In some embodiments, the control assembly 130 can be operatively coupled to a remote compute device 155 (e.g., a mobile compute device such as a smartphone) via a wired or wireless connection (e.g. Bluetooth connection). In some implementations, the remote server 150, the memory 110, and/or the remote compute device 155 can include a database and be configured to provide information related to carrier materials, carrier material profiles, information related to components in a carrier material (e.g., known boiling points of a volatilizable component in an oil), standardized volumes associated with usage of a vaporizer, standardized quantities of volatilized components, a quantity of aerosols associated with the volatilization of a standard carrier material, vapor pressure, atmospheric pressure, and/or environmental or ambient temperatures associated with usage of a vaporizer at specific geographic locations, etc. In some implementations, the remote server 150, the memory 110, and/or the remote compute device 155 can include a database of materials providing information related to temperatures or temperature ranges at which the carrier material should be vaporized (e.g., as determined by a manufacturer of the vaporizer 100A, a manufacturer of the carrier material, and/or a user of the vaporizer 100A). The control assembly 130 can be configured to access the database and control the heating assembly 120 based, at least in part, on information provided in the database. In some instances, the remote compute device 155 can include a user interface including one or more control items and one or more display items configured to perform functions associated with communication with the vaporizer 100B, remote control of the vaporizer 100B, and/or display information associated with functioning or usage of the vaporizer 100B.

Figure 1B:
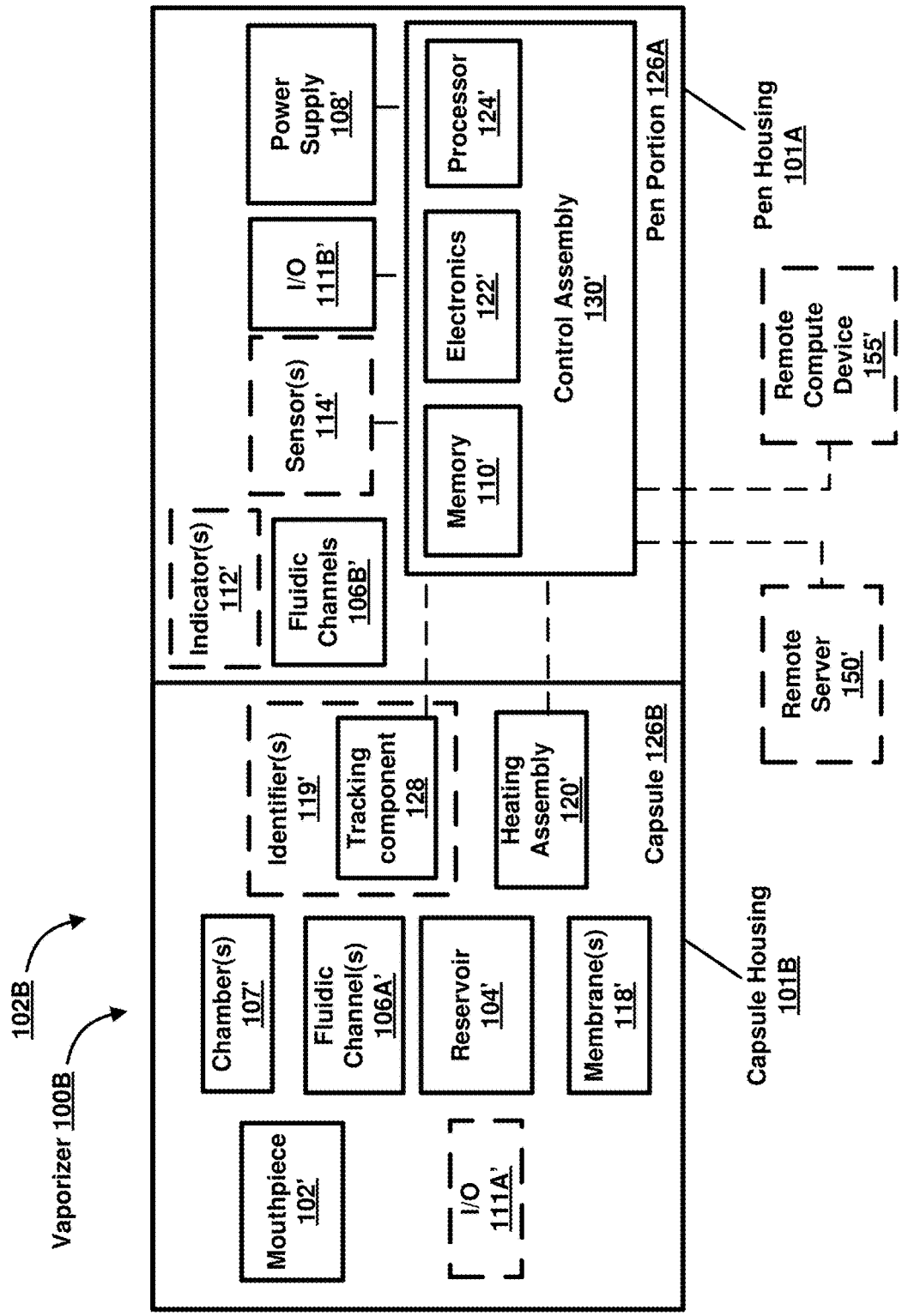
FIG. 1B is a schematic block diagram of a reusable vaporizer, according to an embodiment.

FIG. 1B is a schematic block diagram of a system 102B including a reusable vaporizer, according to an embodiment. As shown in FIG. 1B, a reusable vaporizer 100B includes a pen portion 126A and a capsule portion 126B. The pen portion 126A and the capsule portion 126B of the reusable vaporizer 100B can collectively include components that are the same or similar in structure and/or function to the components of the vaporizer 100B described above. For example, the capsule portion 126B (also referred to as a "capsule," a "capsule assembly," or a "cartridge") includes a mouthpiece 102', a precursor reservoir 104', one or more fluidic channels 106A', one or more chambers 107', a heating assembly 120', membrane(s) 118', an optional input/output (I/O) module 111A', one or more identifiers 119', and optional sensor(s) 114', all disposed within a capsule housing 101B. The one or more identifiers 119' can optionally include a tracking component 128. The pen portion 126A includes a control assembly 130', one or more fluidic channels 106B', a power supply 108', an input/output (I/O) module 111B', and optional indicator(s) 112', all disposed within a pen housing 101A. The control assembly 130' can include a memory 110', electronics 122', and a processor 124', and optionally can be configured to communicate with a remote server 150' and/or a remote compute device 155'. The pen portion 126A (i.e., the pen housing 101A and its contents) can also be referred to as a "battery portion" of the vaporizer 100B. The capsule 126B can be manufactured, shipped and/or sold separately from the pen portion 126A, and assembled by a user to form the vaporizer 100B.

To assemble the vaporizer 100B, a user may, prior to use (e.g., upon purchase of a new capsule), connect the capsule 126B with the pen portion 126A of the vaporizer 100B. The capsule 126B and the pen portion 126A can be configured to be mechanically and electrically connected, for example by one or more of screw attachment, press-fit attachment, snap-fit attachment, magnetic attachment, or any other suitable connection means. As can be inferred from the foregoing, the pen portion 126A can be considered to be a reusable portion of the vaporizer 100B, and the capsule 126B can be considered to be a disposable or "replaceable" portion of the vaporizer 100B. The identifier(s) 119' can include, for example, a bar code, a QR code, and/or a near-field communication (NFC) device such that the vaporizer 100A may be identified and/or recognized by an external device (e.g., the remote compute device 155) and/or the pen portion 126A. For example, the control assembly 130' can be configured to be coupled to the tracking component 128 when the capsule 126B is coupled to the pen portion 126A such that the control assembly 130' can access information contained in the tracking component 128. The tracking component 128 may be, for example, an integrated circuit (e.g., Application-Specific Integrated Circuits (ASICs)). The tracking component 128 can be configured to contain data related to the capsule 126B. In some implementations, the tracking component 128 may contain capsule identification information corresponding to the capsule 126B such that the control assembly 130' may recognize the capsule 126B and such that information about the contents of the capsule 126B can be received from the tracking component 128 by the processor 124'.

To assemble the vaporizer 100B, a user may, prior to use (e.g., upon purchase of a new capsule), connect the capsule assembly 126B with the pen assembly 126A of the vaporizer 100B. The control assembly 130' of the vaporizer 100B can be coupled using any suitable connection such that the control assembly 130' can receive information from the tracking component 128, the remote server 150', and/or the remote compute device 155'. For example, the control assembly 130' can be coupled to the tracking component 128 via a connection subassembly (not shown) which may be coupled to or included within the control assembly 130'. The connection subassembly can include, for example, connectors (e.g., pogo pins) coupled to or included in a printed circuit board such that the control assembly 130' can access information contained in the tracking component 128.

In some implementations, the tracking component 128 may contain information related to the specific carrier material disposed in the reservoir 106A'. In some implementations, the tracking component 128 may provide information related to an identity of the specific carrier material or specifying a particular temperature or temperature range to which the heating element of the heating assembly 120' should be heated by the control assembly 130' (e.g., via applying a particular current to the heating element. The information from the tracking component 128 may be used to generate a heating profile associated with the specific carrier material disposed in the reservoir 104'. For example, a first carrier material may achieve optimal vaporization characteristics at a first temperature and a second carrier material may achieve optimal vaporization characteristics at a second temperature different from the first temperature. The tracking component 128 may be programmed (e.g., by a manufacturer of the vaporizer 100B, the capsule 126B, and/or the carrier material) based on the carrier material in the reservoir 104' such that the tracking component 128 contains information associated with the particular temperature to which the heating element is to be heated (e.g., target temperature data such as a heating profile).

In some embodiments, a specific heating profile can be stored in the tracking component 128 and provided to the processor 124 when the capsule 126B is operatively coupled to the pen portion 126A. In some embodiments, the processor 124' can be configured to request a specific heating profile associated with the carrier material within the capsule 126B from the compute device 155' and/or the remote server 150' (e.g., via the compute device 155') based on the identification data received from the capsule 126B. In some embodiments, the processor can be configured to send one or more signals to the tracking component 128 (e.g., to an integrated circuit of the tracking component 128) of the capsule 126B such that a specific heating profile is stored in the tracking component 128. For example, in some embodiments, when a capsule 126B is initially coupled with a pen portion 126A (and has not been previously coupled with a pen portion 126B since being filled with carrier material), a processor 124' of the pen portion 126B can retrieve information (e.g., a specific heating profile) specific to the carrier material and store the information (e.g., write or program the information) on the tracking component 128 of the capsule 126B. For any subsequent uses of the capsule 126B, the processor 124' of the pen portion 126A (or a processor of another pen portion to which the capsule 126B may be coupled), can retrieve the information specific to the carrier material in the capsule 126B (e.g., the specific heating profile) from the tracking component 128 of the capsule 126B, rather than from the compute device 155' and/or a remote server 150'.

As another example, the control assembly 130' can be coupled via a wired (e.g., Ethernet connection) or a wireless connection (e.g., via a WiFi network connection) to a remote server 150'. The control assembly 130' can also be operatively coupled to a remote compute device 155' (e.g., a mobile compute device such as a smartphone) via a wired or wireless connection (e.g. Bluetooth connection). In some implementations, the remote server 150', the memory 110', and/or the remote compute device 155' can include a database and be configured to provide information related to carrier materials, carrier material profiles, information related to components in a carrier material (e.g., known boiling points of a volatilizable component in an oil), standardized volumes associated with usage of a vaporizer, standardized quantities of volatilized components, a quantity of aerosols associated with the volatilization of a standard carrier material, vapor pressure, atmospheric pressure, and/or environmental or ambient temperatures associated with usage of a vaporizer at specific geographic locations, etc. In some implementations, the remote server 150', the memory 110', and/or the remote compute device 155' can include a database of materials providing information related to target temperature data (e.g., heating profiles, temperatures, or temperature ranges) at which the carrier material should be vaporized (e.g., as determined by a manufacturer of the vaporizer 100A or a component of the vaporizer 100A, a manufacturer of the carrier material, and/or a user of the vaporizer 100A). The control assembly 130' can be configured to access the database and control the heating assembly 120' based, at least in part, on information provided in the database. In some instances, the remote compute device 155' can include a user interface including one or more control items and one or more display items configured to perform functions associated with communication with the vaporizer 100B, remote control of the vaporizer 100B, and/or display information associated with functioning or usage of the vaporizer 100B.

In some embodiments, any of the control assemblies or processors of control assemblies described herein (e.g., the processor 124 or the processor 124') can be configured to receive target temperature data associated with the carrier material (e.g., a heating profile) from a remote server and/or remote computer device, such as any of the remote servers or remote compute devices described herein. For example, the target temperature data can be provided to the control assembly in response to a remote server or remote compute device receiving identification information associated with the carrier material (e.g., identification information of an identifier 119 associated with the carrier material in a reservoir associated with a vaporizer 100A). The control assembly can then supply current to a heating assembly (e.g., the heating assembly 120 or heating assembly 120') based on the target temperature data in response to a user applying suction to a mouthpiece of a vaporizer associated with the control assembly or processor.

In use, a user can draw fluid through the mouthpiece opening 102' by applying the user's mouth to the mouthpiece 102' and applying negative pressure to the mouthpiece opening (e.g., by sucking). In implementations including a pressure sensor (e.g., of the sensor(s) 114') in communication with the control assembly 130', the negative pressure can trigger the pressure sensor. In response to receiving an indication of negative pressure from the pressure sensor (indicated that flow is occurring through the mouthpiece opening), the control assembly 130' may actuate heater control circuitry of the control assembly 130' such that a current is passed to a heating element (e.g., a coil) of the heating assembly 120' (e.g., via a connector subassembly including, for example, pogo pins). Alternatively, in implementations including an activation button in communication with the control assembly 130', the user can actuate the activation button such that the control assembly 130', in response to receiving an actuation signal from the activation button, may actuate heater control circuitry of the control assembly 130' such that a current is passed through the heating element and the heating element is heated to a particular temperature. One or more characteristics of the current or affecting the delivery of the current passed through the heating element (e.g., voltage, wattage) can be controlled by the processor 124' based on, for example, an ambient temperature measured by a temperature sensor of the sensor(s) 114', a resistance of the heating element, and/or a heating profile or target temperature range associated with the carrier material (e.g., as determined by the processor 124' and/or provided to the processor 124' prior to use).

In some embodiments, the control assembly 130' can be configured to determine the contents of the carrier material, including any specific constituent substances, along with particular characteristics of the content (e.g., a boiling point and/or combustion point of each constituent substance). Based at least in part on the characteristics of the contents of the carrier material, the control assembly 130' can determine a particular temperature or temperature range at which the carrier material is to be vaporized. The determination of the particular temperature of temperature range at which the carrier material is to be vaporized may also be based, at least in part, on a desired effect (e.g., taste or physical reaction to inhalation) as communicated to the control assembly 130' via the remote server 150', the remote compute device 155', or the tracking component 128. Based on the particular temperature or temperature range at which the carrier material is intended to be vaporized, upon receiving an indication that a user is applying suction to the mouthpiece opening of the mouthpiece 102' (e.g., via activation of a pressure sensor or a mechanical button), the control assembly 130' can apply a current to the heating element of the heating assembly 120' such that the temperature of the carrier material disposed near the heating element rises to the particular temperature or to a temperature within the particular temperature range. During a period of continuous suction on the mouthpiece opening (e.g., a draw), the control assembly 130' can continue to apply current to the heating element at intervals (e.g., predefined intervals) such that the temperature of the carrier material disposed near the heating element remains within the temperature range determined by the control assembly 130'. For example, the control assembly 130' can control the current and voltage applied to the heating element such that the heat generated by the heating element maintains the temperature of the vaporizing carrier material at a temperature within a particular percentage (e.g., ±1%, ±2%, ±3%, ±4%, ±5%, ±6%, ±7%, ±8%, ±9% or ±10%) of a target temperature. In some embodiments, the control assembly 130' can control the current and voltage applied to the heating element such that the heat generated by the heating element maintains the temperature of the vaporizing carrier material at a temperature that is at least about 1 degree less than the target temperature, at least about 2 degrees less than the target temperature, at least about 3 degrees less than the target temperature, at least about 4 degrees less than the target temperature, at least about 5 degrees less than the target temperature, at least about 6 degrees less than the target temperature, at least about 7 degrees less than the target temperature, at least about 8 degrees less than the target temperature, at least about 9 degrees less than the target temperature, or at least about 10 degrees less than the target temperature. Upon receiving an indication that the user ceased applying suction to the mouthpiece or after a predetermined period of time (e.g., a preset time interval for a draw), the control assembly 130' can discontinue applying current to the heating element such that the carrier material disposed near the heating element cools below the particular temperature or temperature range.

In some embodiments, if the control assembly 130' receives an indication that the user is applying suction to the mouthpiece opening (e.g., via activation of a pressure sensor or a mechanical button) before the carrier material disposed near the heating element has fully cooled to an ambient temperature since the last application of heat to the heating element, the control assembly 130' can apply current to the heating element such that the temperature of the carrier material disposed near the heating element will rise to the particular temperature or to a temperature within the particular temperature range previously determined by the control assembly. For example, the control assembly 130' can determine an amount and characteristics of a current to apply to the heating element and/or a duration of application of the current to the heating element such that the temperature of the carrier material disposed near the heating element will rise to the particular temperature or to a temperature within the particular temperature range previously determined by the control assembly 130'. The control assembly 130' can determine the amount of current to apply to the heating element and/or the duration of application of the current to the heating element based, at least in part, on the current temperature of the heating element and/or on the characteristics of the current previously applied (e.g., the amount and duration of each application) and the elapsed time since the most recently applied current was ceased. Thus, the control assembly 130' can avoid the temperature of the heating element (and the portion of the carrier material disposed near and/or vaporized by the heating element) from continuing to rise over time with each application of current associated with each draw by the user, as demonstrated in FIG. 4, which may result in a change in the user experience from an earlier draw to a later draw due to the carrier material being vaporized at a higher temperature. Instead, the control assembly 130' can account for previous draws and associated heating cycles such that each subsequent draw has vaporization characteristics consistent with earlier draws.

In some embodiments, the control assembly 130' can be configured to heat the carrier material disposed near the heating element to a particular temperature based on a current profile generated based on a heating profile. The current profile, for example, can include an amount of current to be applied over a first duration of time to raise the temperature of the carrier material disposed near the heating element to a vaporization temperature. The current profile can also include an amount of current to be applied for a second duration of time smaller than the first duration at particular intervals to maintain the temperature of the carrier material disposed near the heating element within a vaporization temperature range during a draw by the user (e.g., for several seconds). The intended vaporization temperature, vaporization temperature range, and rate of temperature increase can each be defined by the heating profile. The pressure sensor in combination with the control assembly 130' can be configured to determine the flow rate of the flow through the mouthpiece opening. In some embodiments, the current provided to the heating element may be based, at least in part, on the flow rate and/or duration of flow as determined based on the change in pressure sensed by the pressure sensor. In some embodiments, the current provided to the heating element may be based, at least in part, on the flow rate and the ambient temperature of the vaporizer 100B as measured by a temperature sensor of the sensors (114). For example, prior to an initial use of the vaporizer 100B (e.g., a first draw after installing the capsule 126B or after a sufficiently long time period for the carrier material disposed near the heating element to have cooled to a temperature matching an ambient temperature external to the vaporizer 100B), the carrier material in the reservoir 104' and the heating element can each have a temperature equal to the ambient temperature. The ambient temperature reading by the temperature sensor may be affected by a specific location of the vaporizer 100B (e.g., the vaporizer 100B may be warmer in a pocket of the user due to body heat than if disposed on a table near the user). The control assembly 130' can base the current applied to the heating element at least in part on the ambient temperature such that the proper amount of current is applied to raise the temperature of the heating element (and, thus, the carrier material disposed near the heating element) to the proper vaporization temperature from the ambient temperature (without the temperature being raised too high or too low). Thus, the control assembly 130' can apply more current to the heating element if the ambient temperature is determined to be a first temperature and less current to the heating element if the ambient temperature is determined to be a second temperature higher than the first temperature. As another example, the control assembly 130' can also base the current applied to the heating element at least in part on the ambient temperature by accounting for the effect of the temperature of the air drawn over or near the heating element during a draw by the user. For example, if the vaporizer 100B is used in a cool or cold environment and/or the flow rate of the air is higher, the air passing through the fluidic channel(s) 106A' and over or near the heating element (e.g., a coil) may cause a temperature of the heating element to reduce more than if the vaporizer 100B is used in a warmer environment and/or the flow rate of the air is lower. Thus, the control assembly 130' can apply more current to the heating element if the ambient temperature is determined to be a first temperature and the flow rate of the air through the vaporizer 100B is determined to be a first flow rate and the control assembly 130' can apply less current to the heating element if the ambient temperature is determined to be a second temperature higher than the first temperature and the flow rate of the air through the vaporizer 100B is determined to be a second flow rate lower than the first flow rate.

In some implementations, for example, the control assembly 130' may be configured to heat the carrier material disposed near the heating element to a temperature ranging between about 250 degrees Celsius and about 500 degrees Celsius. In some implementations, for example, the control assembly 130' may be configured to heat the carrier material disposed near the heating element to a temperature ranging between about 200 degrees Celsius and about 450 degrees Celsius.

In some embodiments, the systems 102A and/or 102B in FIGS. 1A and 1B can be substantially the same or similar in structure and/or function to any of the systems described in the U.S. patent application Ser. No. 16/655,153, filed on Oct. 16, 2019, published as US2020/0113246, entitled "Variable-Viscosity Carrier Vaporizers with Enhanced Thermal and Hydrodynamic Properties" (referred to herein as the '153 application) which is incorporated by reference herein in its entirety, for all purposes.

Figure 2:
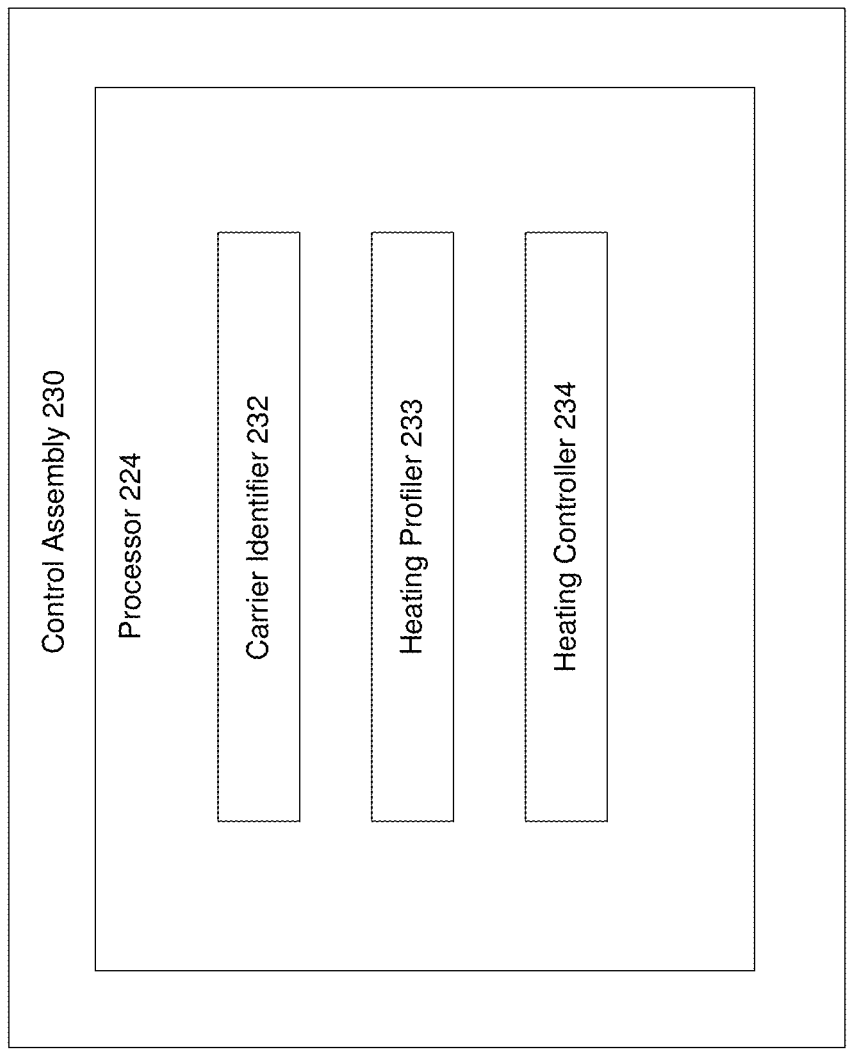
FIG. 2 is a schematic block diagram of a control assembly, according to an embodiment.

FIG. 2 is a schematic illustration of a control assembly 230 of a vaporizer, according to an embodiment. The control assembly 230 can be the same or similar in structure and/or function to any of the control assemblies described herein, such as the control assembly 130 and/or the control assembly 130'. For example, the control assembly 230 includes a processor 224. The processor 224 can be substantially similar in structure and/or function to the processor 124 and/or the processor 124' described above, and/or the processors described in the '153 application incorporated by reference above. The processor 224 can include a carrier identifier 232, a heating profiler 233, and a heating controller 234. The carrier identifier 232 can be configured to generate a carrier material profile associated with carrier material disposed in a reservoir of the vaporizer. The heating profiler 233 can be configured to generate a heating profile based, at least in part, on the carrier material profile. The heating profile can include target heating parameters for vaporization of the carrier material. The heating controller 234 can be configured to control a temperature of the carrier material disposed near a heating element of a heating assembly of the vaporizer such that the carrier material is vaporized according to the parameters defined by the heating profile.

In some embodiments, the carrier identifier 232 can be configured to be operatively coupled to a tracking component that is the same as or similar to the tracking component 128 described above. For example, the carrier identifier 232 can be connected to a tracking component of a capsule assembly included in or coupled to (e.g., engaged with) a pen assembly of the vaporizer via one or more connectors (e.g., pogo pins) associated with a connection subassembly (not shown) of the control assembly 230. The carrier identifier 232 can receive, from the tracking component, data related to the capsule assembly. For example, the carrier identifier 232 can be configured to receive capsule identification information corresponding to the capsule assembly such that the control assembly 230 may recognize the capsule identification information. In some embodiments, the capsule identifying information can include an indication of an identity of the carrier material and/or characteristics of the carrier material included in a reservoir of the capsule assembly. In some embodiments, such as in a disposable vaporizer, a memory of the control assembly 230 can include carrier material identifying information (e.g., via being pre-programmed). In some embodiments, such as in a disposable vaporizer, the vaporizer can include an identifier in communication with the control assembly 230 that provides carrier material identifying information to the carrier identifier 232.

In some embodiments, the vaporizer (e.g., the capsule assembly of the vaporizer) may include one or more additives included with the carrier material and the carrier identifier 232 can receive information identifying the one or more additives and/or characteristics of the one or more additives from the tracking component. The carrier identifier 232 can generate a suitable carrier profile based, at least in part, on the identifying information and/or characteristics associated with the one or more additives.

In some embodiments, the control assembly 230 may be configured to wirelessly communicate with a remote server and/or a remote compute device. The control assembly 230 can transmit the carrier material identification information and/or characteristics and/or capsule identification information to the remote server and/or the remote compute device. In response to receiving carrier material identification information and/or characteristics and/or capsule identification information (e.g., from the control assembly 230), the remote server and/or the remote compute device can send the control assembly 230 additional information, such as information about a capsule assembly coupled to the control assembly 230, information about the carrier material, and/or operation instructions for a heating assembly of the vaporizer based, at least in part, on the carrier material identification information and/or capsule identification information.

In some embodiments, the carrier material profile can include a listing of a set of substances (e.g., compounds) included in the carrier material (including one or more additives if applicable). The carrier material, like any of the carrier materials described herein, can be and/or include any suitable material (e.g., an oil) configured to be vaporized and inhaled by a user. For example, the carrier material can include *Cannabis*, nicotine, propylene glycol, plant-based oils, and/or pharmaceuticals configured to be vaporized for inhalation. Specifically, in some embodiments, the carrier material can include any number of substances including phytocannabinoids, terpenes, and/or other substances that can be volatilized.

Figures 3, 4:
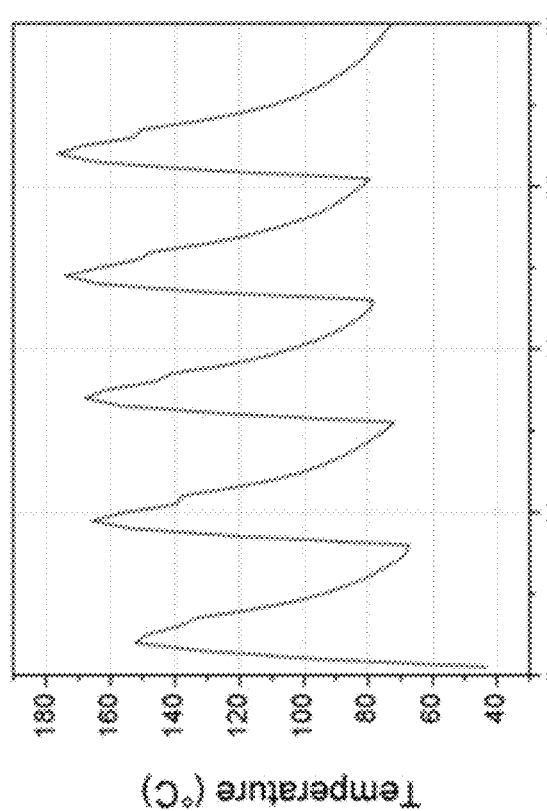
FIG. 3 is a table illustrating the varied boiling points associated with a set of example phytocannabinoids and terpenes that may be included in an example vaporizable liquid.
FIG. 4 is a plot illustrating an example temperature profile, during an instance of usage, of a heating element associated with a vaporizer, according to an embodiment.
Figure 5:
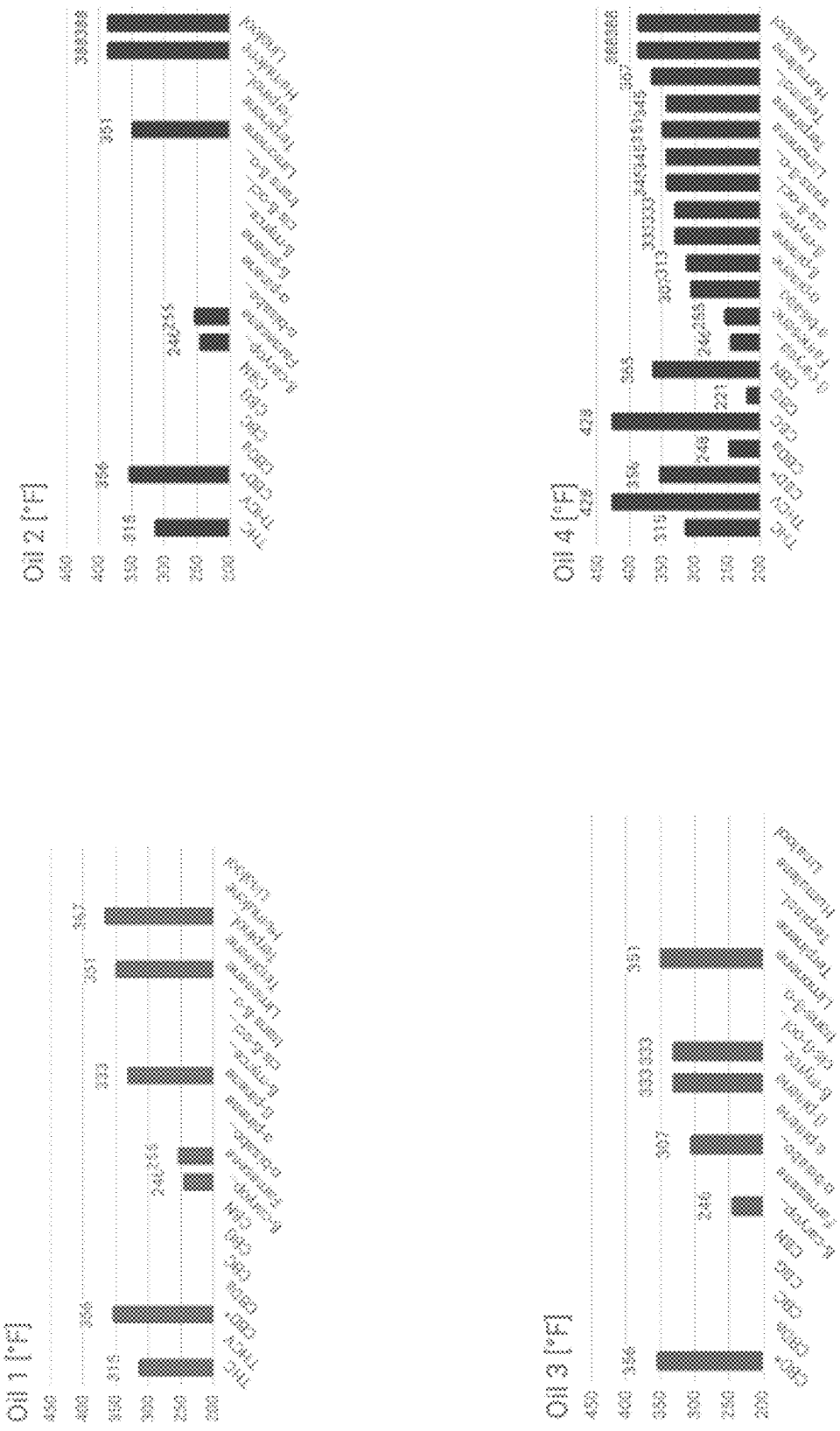
FIG. 5 is a schematic illustration of four charts demonstrating the constituent substances and respective boiling points of the constituent substances of four example carrier materials, according to an embodiment.

The carrier material can include different substances (e.g., compounds included in liquid mediums such as plant-based oils) having different boiling temperatures, combustion temperatures, temperature sensitivities, or temperature ranges associated with different drug efficacy levels. For example, FIG. 3 shows a table 300 listing eighteen example constituent substances and a boiling point or range associated with each substance. Specifically, the table 300 includes nine example phytocannabinoids and nine example terpenes that can be included in a carrier material (e.g., oil). The nine example phytocannabinoids include tetrahydrocannabinol (THC), Delta-8 tetrahydrocannabinol (Δ-8-THC), tetrahydrocannabivarin (THCV), cannabidiol (CBD), cannabidiolic acid synthase (CBDA), Cannabidivarin (CBDV), Cannabinol (CBN), Cannabichromene (CBC), and Cannabigerol (CBG). The nine example terpenes include citronellol, d-limonene, famesene, humulene, linalool, β-caryophyllene, β-myrcene, β-pinene, and terpineol-4-ol. FIG. 5 illustrates four charts demonstrating the constituent substances and respective boiling points of the constituent substances of four example carrier materials (referred to as "Oil 1," "Oil 2," "Oil 3," and "Oil 4"). Each carrier material profile is represented as a bar chart showing the comparative boiling points of each constituent substance of each carrier material. As shown, Oil 3 includes the fewest constituent substances and Oil 4 includes the most constituent substances, each constituent substance having a different boiling point.

The carrier material profile generated by the carrier identifier 232 can include an identification of the particular set of substances included in the carrier material and the boiling point of each constituent substance included in the carrier material. Although not shown, in some embodiments, the carrier material profile can also include the proportion of each substance of the carrier material. In some embodiments, the carrier material profile can also include the viscosity of the carrier material.

In addition to having different temperature requirements for vaporization, substances having different boiling temperatures may also have different characteristics (e.g., taste, effect on the user) after being vaporized and/or heated to different temperatures. Carrier materials containing a number of substances can have an improved or varying overall performance when heated to a particular temperature or temperature range. For example, a particular temperature range may result in the carrier material vaporizing properly (e.g., without combusting or some constituent substances vaporizing while leaving others as liquid in the vaporizer), a particular inhalation concentration of substances being produced, and/or a particular effect on the user (e.g., based on a first substance included in the carrier material vaporizing at a temperature significantly above its respective boiling and a second substance included in the carrier material being vaporized close to its boiling point). Additionally, a particular rate of change of the temperature of the carrier material may result in different compounds being inhaled or in changes to the state of a compound being inhaled (e.g., due to burning). Thus, the heating profiler 233 can be configured to generate a heating profile based, at least in part, on the carrier material profile, accounting for the boiling temperature and/or other characteristics of the constituent substances within the carrier material. The heating profile can include target heating parameters for vaporization of the carrier material to achieve a particular effect intended by a manufacturer of the carrier material and/or capsule assembly and/or a particular effect desired by a user of the vaporizer (e.g., as set using a remote compute device wirelessly coupled to the control assembly 230).

The heating profiler 233 can be operatively coupled to the carrier identifier 232 such that the heating profiler 233 can receive the carrier material profile generated by the carrier identifier 232. The heating profile generated by the heating profiler 233 can indicate a desired set-point temperature that a heating element (e.g., a coil) may be controlled to reach to volatilize the carrier material as intended based, at least in part, on manufacturer instructions, user instructions, and/or the carrier material profile. Specifically, the heating profile can be based, at least in part, on the combination of constituent substances and their respective boiling points in the carrier material profile. The heating profiler 233 can be configured to generate the heating profile based on the constituent substances included in a carrier material such that the heating element temperature is neither too low nor too high for vaporization of the carrier material. A temperature that is too low may result in non-volatilized substances, whereas a temperature that is too high may result in partial boiling of the substance and/or partial combustion of the carrier material which may in turn release unwanted aerosols, creating both health issues and a poor user experience (e.g., a bad taste, a burning sensation in the user's throat, inhalation causing the user to cough, etc.). In some embodiments, the heating profile can be based, at least in part, on a particular desired temperature of vaporization of one or more of the constituent components of the carrier material. For example, a user may prefer the effects of inhaling one or more constituent components vaporized at a first temperature compared to the effects of inhaling the constituent component(s) at a second temperature higher or lower than the first temperature. In some embodiments, the user may be able to indicate the a desired effect or temperature range using, for example, a remote compute device associated with the vaporizer including the control assembly 230 and the heating profiler 233 may be configured to generate the heating profile based, at least in part, on the user's indicated preference.

The heating profile (and any of the heating profiles described herein) can include parameters associated with multiple phases. For example, the heating profile can include a ramp-up or heating phase in which the temperature of the heating element (or the temperature of the carrier material disposed near the heating element) rises to a vaporization temperature. In some embodiments, the ramp-up phase can be configured to initiate upon activation of a pressure sensor of a vaporizer (e.g., caused by a draw on a mouthpiece opening of the vaporizer by a user). After the ramp-up phase, the heating profile can include a set-point phase or a plateau phase (also referred to as a body phase) in which the temperature of the heating element (or the temperature of the carrier material disposed near the heating element) is maintained at the vaporization temperature or within a range of vaporization temperatures such that the carrier material is vaporized for inhalation by the user. In some embodiments, the temperature range may allow the temperature of the heating element to decrease from the beginning to the end of the plateau phase (e.g., decrease 1, 3, 5, 10, 15, 20, 25 degrees, or any suitable interval in between). The plateau phase can be configured to have a duration associated with a duration of an inhalation by a user. For example, the plateau phase can continue until the pressure sensor of the vaporizer senses an increase in pressure above a threshold pressure (e.g., caused by a cessation of the draw on the mouthpiece opening by the user). After the plateau phase, the heating profile can include a ramp-down or a cooling phase in which the temperature of the heating element (or the temperature of the carrier material disposed near the heating element) can cool to a temperature lower than the plateau phase (e.g., a temperature corresponding to the ambient temperature). Each phase can be associated with a set of parameters including a duration, a rate of modulation of temperature, and an amplitude of modulation. The particular parameters of each phase and/or the heating profile may be based, at least in part, on the carrier material profile.

In some embodiments, the heating profiler 233 can use a model heating profile to generate the heating profile. As an example, a heating profiler 233 can generate a model heating profile including a heating phase configured to reach an optimal boiling temperature; a plateau phase configured to maintain the temperature for the duration of the draw; and a cooling phase configured such that a heating element associated with the control assembly 230 cools naturally once the draw has stopped. In some implementations, the heating and plateau phases can be optimized (e.g., via adjusting the durations, temperatures, and rate of temperature increase compared to the model profile) to increase vaporization of the different constituent substances of the carrier material and to decrease combustion or the risk of combustion of one or more of the constituent substances. In some implementations, a user can be provided a set of controls (e.g., via a user interface of a remote compute device wireless coupled to a vaporizer including the control assembly 230) to select different pre-set heating profiles in order to selectively boil one or more of the different substances (i.e., different terpenes and phytocannabinoids) to tune her/his experience.

In some embodiments, the heating profile associated with a carrier material may be based, at least in part, on a set of parameters including usage (e.g., the first or consecutive draws of the vaporizer), ambient conditions, user history, etc. For example, the heating profiler 233 may determine the heating profile based, at least in part, on pre-set user preferences with respect to vaporization temperature and/or inhalation duration. In some embodiments, the various phases of a heating profile can be generated and/or modified by the heating profiler 233 based, at least in part, on environmental conditions. For example, a system can include an environmental temperature sensor that indicates the environmental temperature. The heating profile generated by the heating profiler 233 can be based, at least in part, on the environmental temperature.

The heating controller 234 can be configured to control a temperature of a heating element of a heating assembly of the vaporizer such that the carrier material is vaporized according to the parameters defined by the heating profile by, for example, applying a particular current to the heating element for a particular duration of time such that the temperature of the carrier material disposed near the heating element rises to a particular temperature. In some embodiments, the heating controller 234 can generate a current profile including the characteristics of the current to be applied over time (e.g., over the duration of a user's draw on a vaporizer). For example, the current profile can include an amount and duration of current to be applied during one or more time periods within a duration of a draw or a duration of time including successive, intermittent draws.

In some instances, the heating controller 234 can be configured to modify the current profile, in real-time, based on one or more parameters associated with a usage of the vaporizer. In some implementations, the system may include a flow rate sensor (not shown) in communication with the control assembly 230. The heating controller 234 may be configured to determine a current profile based, at least in part, on the flow rate of air through a portion of the vaporizer caused by a user drawing air through the vaporizer. For example, in some instances when a user employs a longer draw and/or stronger draw, which may cause the heating element to cool beyond a threshold level unless additional current is applied, the heating controller 234 can be configured to take the flow rate and/or duration of the draw into consideration and appropriately modify the current profile, dynamically, in real-time for the next draw in the instance of usage. In some implementations, the control assembly 230 can receive data or generate a record of heating and cooling rate of the heating element in different ambient conditions and under different operation conditions (draw length, draw intensity and draw interval, external temperature and pressure, level or carrier material inside the reservoir, battery life, etc.), based for example, on testing, and determine the heating profile and the current profile based, at least in part, on this data/record.

Additionally, when users repeatedly and consecutively draw on the mouthpiece of the vaporizer within a short time duration (e.g., multiple draws over one or two minutes), a heating element and/or an interior of a vaporizer including the heating element can cumulatively build up heat, causing the temperature of the heating element and/or the vapor produced by the vaporizer to reach higher and higher temperatures. As previously indicated, FIG. 4 illustrates the temperature of a heating element of a vaporizer during an instance of continuing operation including successive draws applied to the vaporizer (e.g., five consecutive draws over 80 seconds), each draw beginning before the carrier material disposed near the heating element had cooled to an ambient temperature after the previous draw. As shown, the maximum and minimum temperatures of the heating and cooling cycle of the carrier material disposed near the heating element rise with each consecutive draw. In some embodiments, to avoid the maximum temperature of the carrier material disposed near the heating element rising with each consecutive draw, the heating controller 234 can generate a current profile indicating the amount of current to be supplied to the heating element (e.g., a coil) associated with the vaporizer to reach the vaporization temperature or temperature range defined by the heating profiler 233 as indicated in the heating profile, the current profile based, at least in part, on the current and heating parameters associated with the previous draw and/or the temperature of the heating element and/or the carrier material disposed near the heating element at the time of the subsequent draw. For example, if a user applies consecutive draws to a mouthpiece of a vaporizer (e.g., each draw is applied before a heating element of a heating assembly of the vaporizer naturally cools to correspond to an ambient temperature), less current is needed to increase the temperature of the heating element to the vaporization temperature for the second draw and subsequent draws compared to the current required for the initial ramp-up phase of the heating element. Thus, the heating profiler 234 can be configured to generate a heating profile that would result in applying current to the heating element to reach the intended temperature (e.g., the vaporization temperature determined by the heating profiler 233) based, at least in part, on the temperature of the heating element and/or the carrier material disposed near the heating element at the time of the second or subsequent draw.

Figure 6:
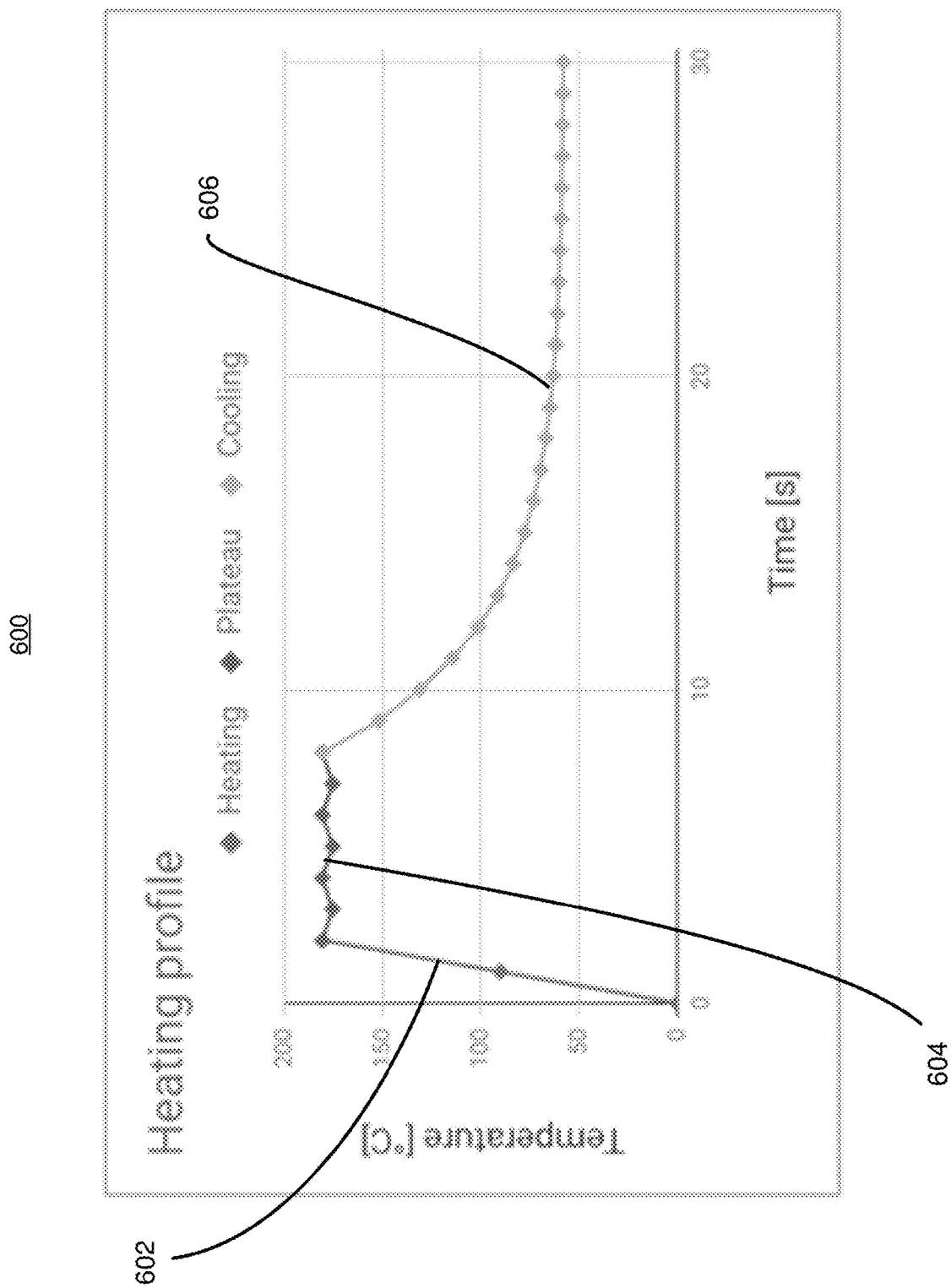
FIG. 6 is a plot of an example heating profile associated with a single draw applied to a vaporizer, according to an embodiment.

FIG. 6 illustrates an example heating profile 600 associated with a single draw during usage of a vaporizer, according to an embodiment. The heating profile 600 is a representative example of a heating profile of a heating element of a heating assembly that can be generated by a control assembly that is the same or similar to any of the control assemblies described herein, such as the control assembly 130, the control assembly 130', and/or the heating profiler 233 of the control assembly 230. As shown in FIG. 6, the heating profile 600 can have a ramp-up or heating phase 602 in which the temperature of the carrier material disposed near the heating element rises. After the heating phase 602, the heating profile 600 can include a set-point phase or a plateau phase 604 in which the temperature of the carrier material disposed near the heating element is maintained at a temperature or within a range of temperatures. The plateau phase 604 can be configured to have a duration associated with a duration of an inhalation by a user. After the plateau phase 604, the heating profile 600 can include a ramp-down or a cooling phase 606 in which the temperature of the carrier material disposed near the heating element can cool to a temperature corresponding to the ambient temperature. Each phase can be associated with a set of parameters including a duration, a rate of modulation of temperature, and an amplitude of modulation. The particular parameters of each phase and/or the heating profile may be based, at least in part, on the carrier material profile. The heating element, which may be the same or similar to any of the heating elements described herein, can be controlled by the control assembly such that the temperature of the carrier material disposed near the heating element is adjusted according to the heating profile shown in FIG. 6 upon activation of the vaporizer for inhalation.

Figure 7:
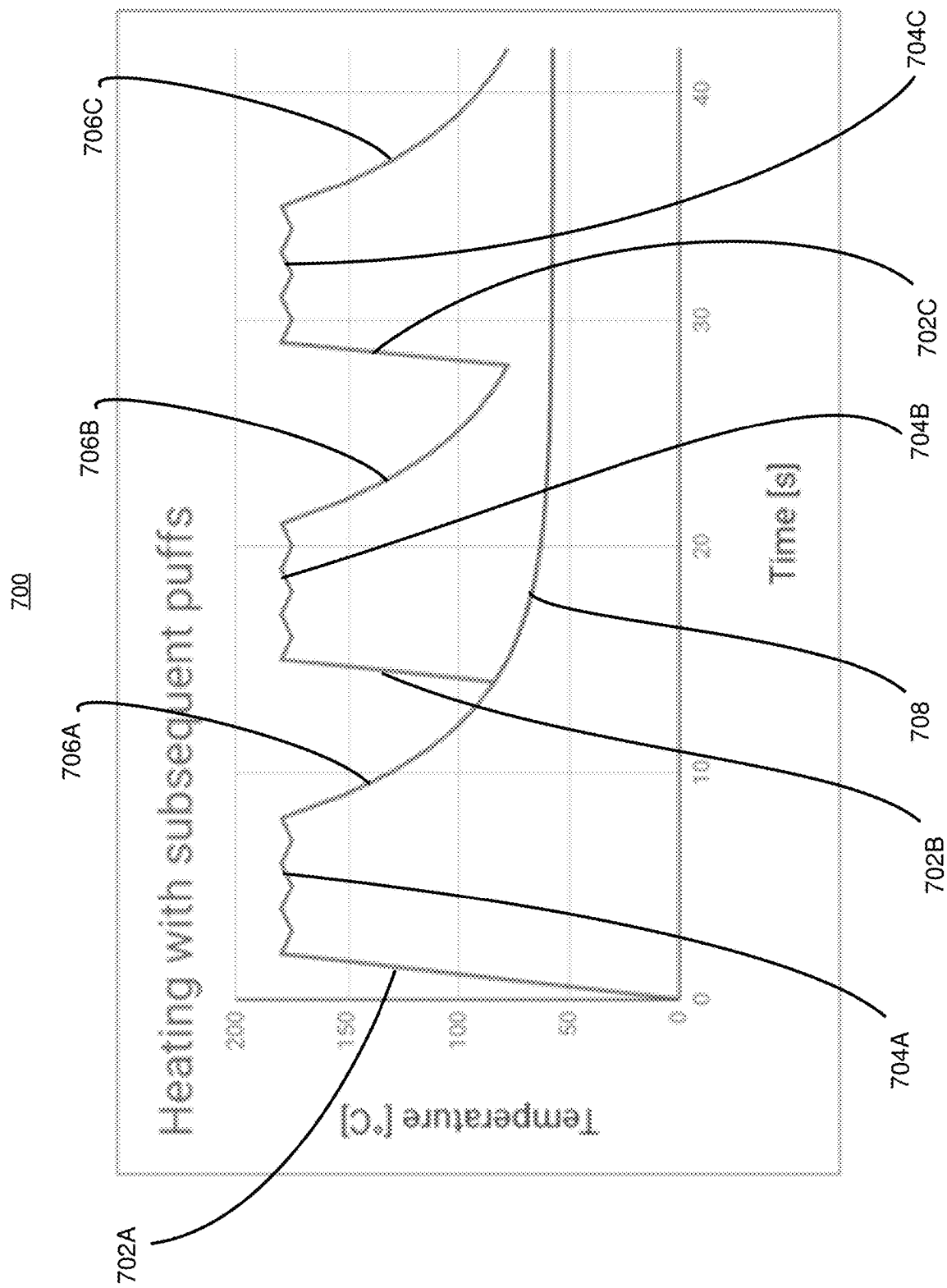
FIG. 7 is a plot of an example heating progression associated with multiple consecutive draws applied to a vaporizer, according to an embodiment.

FIG. 7 illustrates an example of a heating progression 700 associated with a usage including three draws of a vaporizer, according to an embodiment. The heating progression 700 is a representative example of a heating progression of a heating element of a heating assembly under the control of a control assembly that is the same or similar to any of the control assemblies described herein, such as the control assembly 130, the control assembly 130', and/or the heating controller 234 of the control assembly 230. As shown in FIG. 7, under control of the control assembly (e.g., heater circuitry of the control assembly), the heating element can have an initial ramp-up or heating phase 702A in which the temperature of the carrier material disposed near a heating element rises. After the initial heating phase 702A, the heating progression 700 can include a first set-point phase or a plateau phase 704A in which the temperature of the carrier material disposed near the heating element is maintained at a temperature or within a range of temperatures such that a carrier material of the vaporizer disposed adjacent to the heating element is vaporized. The plateau phase 704A can be configured to have a duration associated with a duration of the first draw by a user. After the plateau phase 704A (e.g., when the first draw has ceased), the heating progression 700 can include a first ramp-down or a cooling phase 706A in which the temperature of the carrier material disposed near the heating element can cool toward a temperature corresponding to the ambient temperature.

If the user applies a second draw on the vaporizer, before the temperature of the heating element has cooled to the ambient temperature, the control assembly can apply an amount of current and/or duration of current to the heating element such that the temperature of the carrier material disposed near the heating element rises as represented by a second heating phase 702B. The amount of current and/or duration of current applied can be based, at least in part, on the temperature of the heating element at the time of the second draw. Thus, instead of applying the same amount of current for the same duration as applied during the initial heating phase 702A (which would result in the temperature of the carrier material disposed near the heating element rising to a temperature above the intended vaporization temperature), the temperature of the carrier material disposed near the heating element can be raised during the second heating phase 702B to the same temperature or temperature range as the first plateau phase 704A. The heating element can then be maintained in a second set-point phase or a plateau phase 704B in which the temperature of the carrier material disposed near the heating element is maintained at a temperature or within a range of temperatures such that a carrier material of the vaporizer disposed adjacent to the heating element is vaporized. The plateau phase 704B can be configured to have a duration associated with a duration of the second draw by a user. After the second plateau phase 704B (e.g., when the second draw has ceased), the heating progression 700 can include a second ramp-down or a cooling phase 706B in which the carrier material disposed near the temperature of the heating element can cool toward a temperature corresponding to the ambient temperature.

If the user applies a third draw on the vaporizer, before the temperature of the carrier material disposed near the heating element has cooled to the ambient temperature, the control assembly can apply an amount of current and/or duration of current to the heating element such that the temperature of the carrier material disposed near the heating element rises as represented by a third heating phase 702C. The amount of current and/or duration of current applied can be based, at least in part, on the temperature of the carrier material disposed near the heating element at the time of the third draw. The temperature of the carrier material disposed near the heating element can be raised during the third heating phase 702C to the same temperature or temperature range as the first plateau phase 704A and the second plateau phase 704B. The heating element can then be maintained in a third set-point phase or a plateau phase 704C in which the temperature of the carrier material disposed near the heating element is maintained at a temperature or within a range of temperatures such that a carrier material of the vaporizer disposed adjacent to the heating element is vaporized. The plateau phase 704C can be configured to have a duration associated with a duration of the third draw by a user. After the third plateau phase 704C (e.g., when the third draw has ceased), the heating progression 700 can include a third ramp-down or a cooling phase 706C in which the temperature of the carrier material disposed near the heating element can cool toward a temperature corresponding to the ambient temperature. Each phase can be associated with a set of heating and/or current application parameters including a duration, a rate of modulation of temperature, and an amplitude of modulation. The particular parameters of the heating of each phase and/or a heating profile associated with the carrier material and/or the heating element may be based, at least in part, on the carrier material profile.

Figure 8:
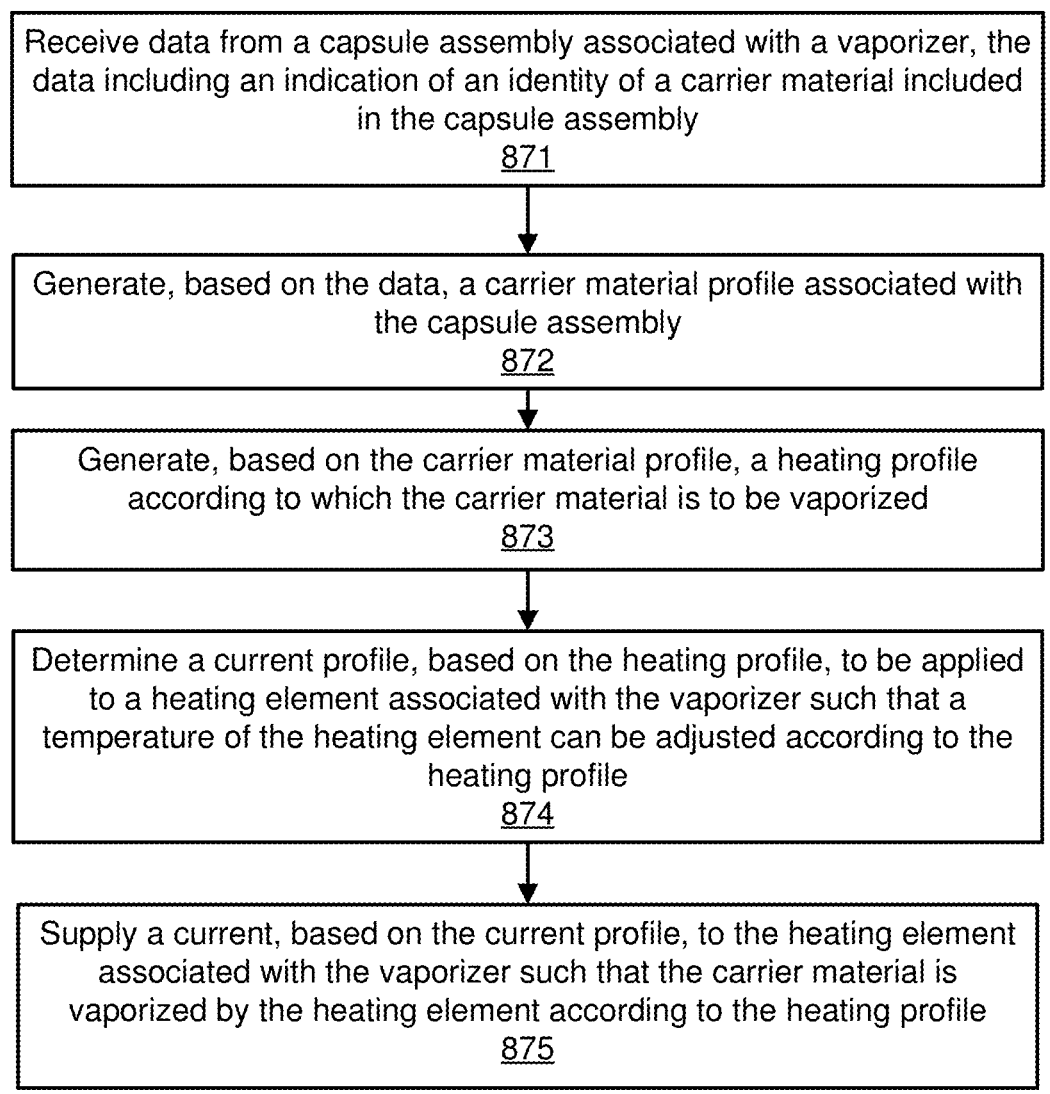
FIG. 8 is a flowchart of an example method of controlling heating of a carrier material by a vaporizer, according to an embodiment.

FIG. 8 is a flowchart describing an example method 800 of controlling a heating element to volatilize a carrier material using a vaporizer, according to an embodiment. The method 800 can be implemented by any suitable vaporizer described herein (e.g., the vaporizer 100A and/or 100B) or any vaporizer described in the '153 application referenced above. In some embodiments, the method 800 can be implemented using a control assembly similar in structure and/or function to any of the control assemblies described herein, such as the control assembly 130, the control assembly 130', and/or the control assembly 230 described above. In some implementations, as described previously, the control assembly can include one or more processors operatively coupled to a memory, the one or more processors configured to implement the method 800.

A processor implementing the method 800 receives data, at 871, from a capsule assembly associated with a vaporizer, the data including an indication of an identity of a carrier material included in the capsule assembly. In some implementations, the data can be received from a tracking component associated with the capsule assembly. The tracking component may be programmed (e.g., by a manufacturer of the vaporizer or the capsule assembly) to include information related to the specific carrier material disposed in the reservoir associated with the capsule assembly. In some implementations, the tracking component may provide information related to an identity of the specific carrier material and/or the constituent components of the specific carrier material. For example, the tracking component may provide the identity of volatilizable components included in the carrier material such as phytocannabinoids, terpenes, etc. In some embodiments, the method 800 optionally includes receiving data from a remote compute device and/or a remote server related to the characteristics of the carrier material and/or heating instructions.

At 872, the processor generates, based on the data, a carrier material profile associated with the capsule assembly. The carrier material profile can include information received from the capsule assembly. In some embodiments, the carrier material profile can include information received from a remote compute device and/or a remote server. The carrier material profile can include, for example, an identity of the specific carrier material and/or the constituent components of the specific carrier material and characteristics of the specific carrier material and/or the constituent components of the specific carrier material (e.g., boiling points and/or combustion points).

At 873, the processor generates, based on the carrier material profile, a heating profile according to which the carrier material is to be vaporized. In some implementations, in addition to the carrier material profile, the processor can receive information from one or more sensors associated with the vaporizer and use the information from the sensors to generate the heating profile. In some implementations, the processor can use one or more algorithms or routines to use information related to the carrier material profile, and/or the expected usage of the vaporizer to generate the heating profile. For example, the processor can take into consideration the relative amount of volatilizable components indicated in the carrier material profile, the relative boiling points of the components, usage history associated with a vaporizer (e.g., recent use history), ambient conditions (e.g., ambient temperature, ambient pressure), current temperature of the heating element or the carrier material disposed near the heating element, etc. In some implementations, the processor can generate the heating profile based, at least in part, on a vaporization temperature and/or intended inhalation-related effect desired by a user and/or manufacturer of the carrier material, capsule assembly, and/or vaporizer.

At 874, the processor determines, based on the heating profile, a current profile configured to be applied to a heating element (e.g., a coil) associated with the vaporizer such that a temperature of the carrier material disposed near the heating element can be adjusted according to the heating profile. In some implementations, the processor can be configured to actuate heater control circuitry associated with the control assembly of the vaporizer such that a current is passed, according to the parameters of the current profile, to the heating element. In some implementations, the processor can generate the current profile based, at least in part, on specifications and/or properties of the heating element. In some instances, the processor can receive a set of inputs associated with an instance of a usage of the vaporizer and generate the current profile based on the inputs.

At 875, the method 800 includes supplying a current based on the current profile to the heating element associated with the vaporizer. The current may be supplied via the heater control circuitry associated with the control assembly. In some implementations, the heater control circuitry may be configured to control the temperature of the carrier material disposed near the heating element using a feedback mechanism. For example, the heater control circuitry can receive, from one or more temperature sensors, a report of the temperature of the heating element or the carrier material disposed near the heating element at a point in time and can compare the reported temperature with a setpoint temperature higher than the reported temperature, the set point temperature being based on the heating profile. Based on the comparison, the heater control circuitry can determine the difference between the reported temperature and the setpoint temperature and supply a current to the heating element to change the temperature of the heating element to decrease the difference. In some implementations the current profile and/or the current supplied to the heating element may be changed in real-time based on one or more inputs received. For example, in some implementations the control assembly can receive a set of inputs associated with an instance of a usage of the vaporizer, the inputs including parameters of usage (e.g., duration of a draw, a volume associated with a draw, number of preceding draws in the recent usage history, etc.). The current profile can be generated and/or modified in real-time based on the set of inputs.

In some implementations, a user may be able to use a remote compute device (e.g., a mobile device) to set a target temperature of the carrier material disposed near the heating element (e.g., a coil of a heating assembly) prior to or during use. Thus, if the user desires a particular vaporization temperature or a higher or lower vaporization temperature, the user may set the temperature or request a temperature change via the remote compute device. The remote compute device may then send the instructions remotely (e.g., via Bluetooth) to a transceiver associated with the control assembly (e.g., control assembly 230). The control assembly may then adjust the current sent or applied to the heating element via the heater control circuitry according to the instructions sent from the remote compute device.

Figure 9:
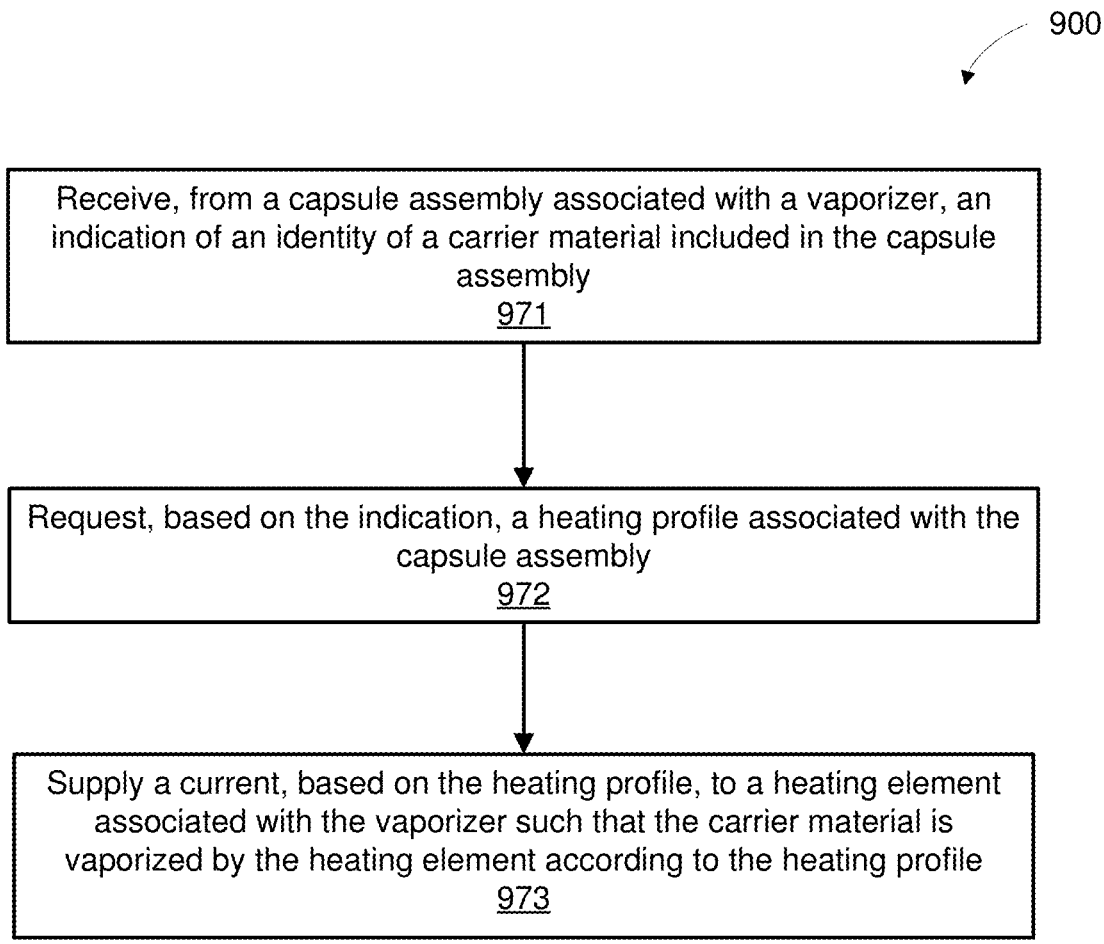
FIG. 9 is a flowchart of an example method of controlling heating of a carrier material by a vaporizer, according to an embodiment.

FIG. 9 is a flowchart describing an example method 900 of controlling a heating element to volatilize a carrier material using a vaporizer, according to an embodiment. The method 900 can be implemented by any suitable vaporizer described herein (e.g., the vaporizer 100A and/or 100B) or any vaporizer described in the '153 application referenced above. In some embodiments, the method 900 can be implemented using a control assembly similar in structure and/or function to any of the control assemblies described herein, such as the control assembly 130, the control assembly 130', and/or the control assembly 230 described above. In some implementations, as described previously, the control assembly can include one or more processors operatively coupled to a memory, the one or more processors configured to implement the method 900.

As shown at 971, an indication of an identity of a carrier material included in a capsule assembly associated with a vaporizer can be received from the capsule assembly. A heating profile associated with the capsule assembly can be requested at 972 based on the indication. The heating profile can be received from, for example, a server (e.g., remote server 150') via a cloud. In some embodiments, the heating profile can be predetermined (e.g., by a manufacturer) and associated with the capsule assembly and/or carrier material prior to attachment of the capsule assembly to a pen portion of the vaporizer. The heating profile can include a target temperature or temperature range (e.g., a percentage range from the target temperature) at which the carrier material is to be vaporized, a specific rate of temperature increase of the carrier material to be vaporized, a duration of a temperature ramp-up period, a duration of a vaporization or plateau period at which the carrier material is vaporized at the target temperature or within the target temperature range, and/or any other suitable characteristic of a heating profile described herein.

A current can be supplied at 973 to a heating element associated with the vaporizer based on the heating profile such that the carrier material is vaporized by the heating element according to the heating profile. The current can be supplied based on the target temperature of the carrier material disposed near the heating element over the duration of use of the vaporizer according to the heating profile, a resistance of the heating element, an ambient temperature of the vaporizer as measured by a temperature sensor of the vaporizer, a temperature of the heating element (e.g., if the heating element is already above ambient temperature, less current needs to be applied to the heating element to reach the same target temperature than if the heating element is at ambient temperature), a flow rate of air through the vaporizer (as determined based on, for example, a change in pressure over time as measured by a pressure sensor of the vaporizer), particular characteristics of the current (e.g., voltage, wattage), and/or any other factors as described herein.

Figure 10:
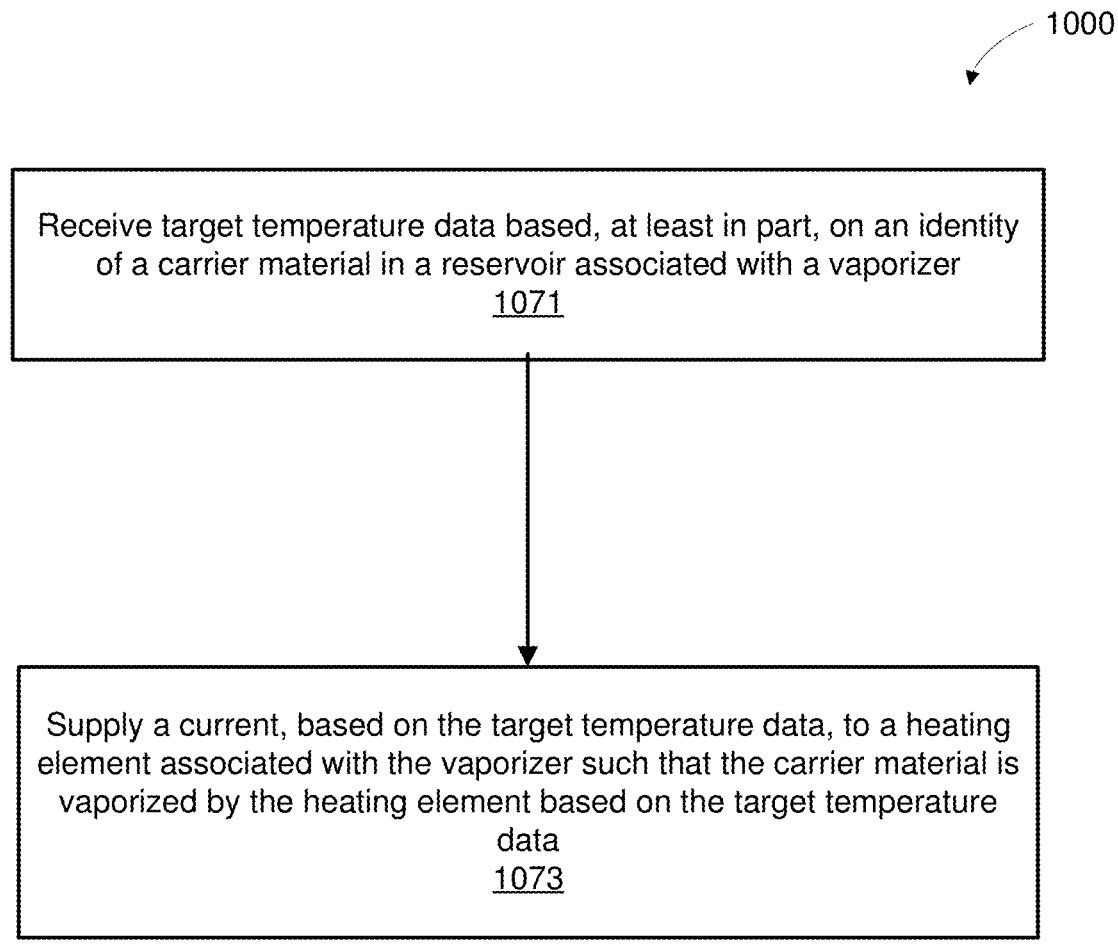
FIG. 10 is a flowchart of an example method of controlling heating of a carrier material by a vaporizer, according to an embodiment.

FIG. 10 is a flowchart describing an example method 1000 of controlling a heating element to volatilize a carrier material using a vaporizer, according to an embodiment. The method 1000 can be implemented by any suitable vaporizer described herein (e.g., the vaporizer 100A and/or 100B) or any vaporizer described in the '153 application referenced above. In some embodiments, the method 1000 can be implemented using a control assembly similar in structure and/or function to any of the control assemblies described herein, such as the control assembly 130, the control assembly 130', and/or the control assembly 230 described above. In some implementations, as described previously, the control assembly can include one or more processors operatively coupled to a memory, the one or more processors configured to implement the method 1000.

As shown at 1071, target temperature data can be received by a control assembly based, at least in part, on an identity of a carrier material contained in a reservoir associated with a vaporizer. A current can be supplied at 1073 by the control assembly to a heating element associated with the vaporizer based on the target temperature data such that the carrier material is vaporized by the heating element according to the target temperature data. In some embodiments, the target temperature data can be received from a remote compute device or a remote server based on an identifier associated with the carrier material being provided to a remote compute device or a remote server. The target temperature data can include, for example, a heating profile associated with the carrier material contained in the reservoir associated with the vaporizer. The heating profile and implementation of the heating profile can be the same or similar in structure and/or function to any of the heating profiles and implementations of heating profiles to control a heating assembly described herein. For example, in some embodiments, the heating profile can be predetermined and associated with a capsule assembly and/or carrier material prior to attachment of the capsule assembly to a pen portion of the vaporizer. In some embodiments, the heating profile can be predetermined and associated with carrier material disposed in a reservoir associated with a vaporizer (e.g., via being disposed within the vaporizer housing or disposed within a capsule assembly coupleable to the vaporizer housing). The heating profile can include a target temperature or temperature range (e.g., a percentage range from the target temperature) at which the carrier material is to be vaporized, a specific rate of temperature increase of the carrier material to be vaporized, a duration of a temperature ramp-up period or portion, a duration of a vaporization or plateau period or portion (also referred to as a body period or portion) at which the carrier material is vaporized at the target temperature or within the target temperature range, and/or any other suitable characteristic of a heating profile described herein.

In some embodiments, such as any of the embodiments described herein, a user can select a particular style of vapor delivery associated with one or more of the constituent substances included in the carrier material using, for example, a user interface disposed on the vaporizer (e.g., a mechanical interface such as a button) and/or using a user interface of a compute device (e.g., any of the compute devices described herein) associated with the vaporizer. For example, a user interface can include three options (e.g., three selection buttons). The selection buttons can be presented, for example, as a slider. The options can allow the user to select one of a first vapor style (e.g., represented as "flavor"), a second vapor style (e.g., represented as "balanced"), and a third vapor style (e.g., represented as "heavy"). The first vapor style can correspond to a first heating profile, the second vapor style can correspond to a second heating profile, and the third vapor style can correspond to a third heating profile. Each of the heating profiles can be based, at least in part, on the carrier material to be used with the vaporizer. In some embodiments, selection of the first heating profile may cause the carrier material to be vaporized at a lower temperature (e.g., through the "body" portion of the draw), resulting in a stronger, fuller, or otherwise improved flavor but a lower dosage of delivered constituent substance(s) per draw, while selection of the third heating profile may cause the carrier material to be vaporized at a higher temperature (e.g., through the "body" portion of the draw), resulting in a weaker or otherwise less intense flavor but a higher dosage of delivered constituent substance(s) per draw. The second heating profile may result in stronger flavor and a higher delivered dosage per draw than the third heating profile and weaker flavor and lower delivered dosage than the first heating profile. Thus, in some embodiments, each carrier material may be associated with three predetermined heating profiles (e.g., predetermined by a manufacturer) such that the user can choose which of the three heating profiles to implement for a particular inhalation or draw based on the preferences of the user.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

In addition, the disclosure may include other innovations not presently described. Applicant reserves all rights in such innovations, including the right to embodiment such innovations, file additional applications, continuations, continuations-in-part, divisional s, and/or the like thereof. As such, it should be understood that advantages, embodiments, examples, functional, features, logical, operational, organizational, structural, topological, and/or other aspects of the disclosure are not to be considered limitations on the disclosure as defined by the embodiments or limitations on equivalents to the embodiments. Depending on the particular desires and/or characteristics of an individual and/or enterprise user, database configuration and/or relational model, data type, data transmission and/or network framework, syntax structure, and/or the like, various embodiments of the technology disclosed herein may be implemented in a manner that enables a great deal of flexibility and customization as described herein.

All definitions, as defined and used herein, should be understood to control over dictionary definitions, definitions in documents incorporated by reference, and/or ordinary meanings of the defined terms.

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The indefinite articles "a" and "an," as used herein in the specification and in the embodiments, unless clearly indicated to the contrary, should be understood to mean "at least one."

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While specific embodiments of the present disclosure have been outlined above, many alternatives, modifications, and variations will be apparent to those skilled in the art. Accordingly, the embodiments set forth herein are intended to be illustrative, not limiting. Various changes may be made without departing from the spirit and scope of the disclosure. Where methods and steps described above indicate certain events occurring in a certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

The invention claimed is:

1. A system, comprising:
a mouthpiece defining a mouthpiece opening;
a reservoir configured to contain carrier material;
a heating assembly including a heating element configured to apply heat to the carrier material; and
a control assembly configured to:
receive target temperature data upon coupling of a cartridge portion to a pen portion, the target temperature data based, at least in part, on an identity of the carrier material contained in the reservoir, the target temperature data including a heating profile based, at least in part, on the identity of the carrier material and associated with a period of continuous suction by a user on the mouthpiece opening, the heating profile including a ramp up portion, a body portion, and a ramp down portion;
upon receiving an indication that a user is applying a first suction to the mouthpiece opening of the mouthpiece, apply a current to the heating element of the heating assembly according to the heating profile such that a temperature of a portion of the carrier material disposed near the heating element rises from a first temperature to a second temperature during a first period associated with the ramp up portion, remains within a predetermined range of the second temperature during a second period associated with the body portion, and decreases from the second temperature to a third temperature during a third period associated with the ramp down portion; and
upon receiving an indication that a user is applying a second suction to the mouthpiece opening of the mouthpiece before the heating element has returned to ambient temperature during the ramp down portion of the application of current to the heating element according to the heating profile, the control assembly is configured to apply an amount of current and/or duration of current to the heating element such that the temperature of the carrier material disposed near the heating element rises to the second temperature, the amount of current and/or the duration of current applied by the control assembly based, at least in part, on a temperature of the heating element at the time of the second suction.

2. The system of claim 1, wherein the control assembly is configured to receive the target temperature data from a remote compute device.

3. The system of claim 1, wherein the control assembly is configured to receive the target temperature data from a remote server.

4. The system of claim 1, wherein the control assembly is disposed within the pen portion.

5. The system of claim 1, wherein the control assembly is configured to receive the target temperature data in response to an identifier associated with the carrier material contained in the reservoir being provided to a remote compute device.

6. The system of claim 1, wherein the target temperature data is based, at least in part, on one or more constituent substances included in the carrier material.

7. A system, comprising:
a mouthpiece defining a mouthpiece opening;
a reservoir configured to contain carrier material;
a heating assembly including a heating element configured to apply heat to the carrier material; and
a control assembly configured to:
receive heating instruction data associated with the carrier material from a memory, and
upon receiving an indication that a user is applying suction to the mouthpiece opening of the mouthpiece, control application of a current to the heating element of the heating assembly for a duration determined by a processor of the control assembly such that a temperature of a portion of the carrier material disposed near the heating element rises to a target temperature, the duration of application of the current based on the received heating instruction data and an elapsed time since a most recently applied current to the heating element was ceased.

8. The system of claim 7, wherein the processor of the control assembly is configured to determine the duration of application of the current based, at least in part, on characteristics of the carrier material.

9. The system of claim 7, further comprising a tracking component, the control assembly configured to determine the duration of application of the current based, at least in part, on identification information associated with the carrier material received from the tracking component.

10. The system of claim 7, wherein the control assembly is configured to determine the target temperature based at least in part on a heating profile associated with a period of continuous suction by a user on the mouthpiece opening, the heating profile including a ramp up portion, a body portion, and a ramp down portion, the control assembly configured to apply current to the heating element according to the heating profile such that the temperature of the carrier material disposed near the heating element rises from a first temperature to a second temperature during a first period associated with the ramp up portion, remains within a predetermined range of the second temperature during a second period associated with the body portion, and decreases from the second temperature to a third temperature during a third period associated with the ramp down portion.

11. The system of claim 10, wherein the heating profile is associated with the carrier material in the reservoir, and the control assembly is configured to receive the heating profile from a remote compute device in response to identification information associated with the carrier material being provided to the remote compute device.

12. The system of claim 7, wherein the control assembly is configured to determine at least one of an amount of the current to apply to the heating element or the duration of application of the current to the heating element based, at least in part, on a current temperature of the heating element.

13. The system of claim 7, wherein the control assembly is configured to determine at least one of an amount of the current to apply to the heating element or the duration of application of the current to the heating element based, at least in part, on one or more characteristics of a most recent previously applied current to the heating element.

14. A system, comprising:
a cartridge portion of a vaporizer device including:
 a mouthpiece defining a mouthpiece opening,
 a reservoir configured to contain carrier material,
 a memory storing heating instruction data, and
 a heating assembly including a heating element configured to apply heat to the carrier material; and
a pen portion of the vaporizer device including a control assembly, the control assembly configured to:
 receive the heating instruction data associated with the carrier material from the cartridge portion upon coupling of the cartridge portion to the pen portion, the heating instruction data associated with the carrier material based, at least in part, on an identity of the carrier material contained in the reservoir; and
 upon receiving an indication that a user is applying suction to the mouthpiece opening of the mouthpiece, control application of a current to the heating element of the heating assembly for a duration determined by a processor of the control assembly such that a temperature of a portion of the carrier material disposed near the heating element rises to a target temperature, the duration or application of the current based on the received heating instruction data and an elapsed time since a most recently applied current to the heating element was ceased.

15. The system of claim 14, wherein the control assembly is configured to receive the heating instruction data from the cartridge portion via an electrical coupling between the pen portion and the cartridge portion.

16. The system of claim 14, wherein the heating instruction data is based, at least in part, on one or more constituent substances included in the carrier material.

17. The system of claim 14, wherein the cartridge portion further comprises a tracking component, the control assembly configured to receive heating instruction data from the tracking component.

18. The system of claim 14, wherein the heating instruction data is assigned to the cartridge portion by a manufacturer of at least one of the carrier material or the cartridge portion, and the control assembly is configured to apply the current to the heating element of the heating element such that the temperature of the carrier material near the heating element is controlled according to the heating instruction data assigned by the manufacturer.

19. A system, comprising:
a mouthpiece defining a mouthpiece opening;
a reservoir configured to contain carrier material;
a heating assembly including a heating element configured to apply heat to the carrier material; and
a control assembly configured to:
 receive heating instruction data upon coupling of a cartridge portion to a pen portion, the heating instruction data based, at least in part, on an identity of the carrier material contained in the reservoir;
 upon receiving an indication that a user is applying a first suction to the mouthpiece opening of the mouthpiece, apply a current to the heating element of the heating assembly according to the heating instruction data such that a temperature of a portion of the carrier material disposed near the heating element rises from a first temperature to a second temperature during a first period associated with a ramp up portion of a heating profile, remains within a predetermined range of the second temperature during a second period associated with a body portion of the heating profile, and decreases from the second temperature to a third temperature during a third period associated with a ramp down portion of the heating profile; and
 upon receiving an indication that a user is applying a second suction to the mouthpiece opening of the mouthpiece before the heating element has returned to ambient temperature during the ramp down portion of the application of current to the heating element according to the heating profile, the control assembly is configured to apply a duration of current to the heating element such that the temperature of the carrier material disposed near the heating element rises to the second temperature, the duration of current applied by the control assembly based, at least in part, on an elapsed time since a most recently applied current to the heating element was ceased.

* * * * *